(12) United States Patent
Lamb et al.

(10) Patent No.: US 12,005,078 B2
(45) Date of Patent: Jun. 11, 2024

(54) GENETICALLY ENGINEERED DRUG RESISTANT T CELLS AND METHODS OF USING THE SAME

(71) Applicants: The UAB Research Foundation, Birmingham, AL (US); Emory University, Atlanta, GA (US); Children's Healthcare of Atlanta, Inc., Atlanta, GA (US)

(72) Inventors: Lawrence S. Lamb, Birmingham, AL (US); H. Trent Spencer, Marietta, GA (US); G. Yancey Gillespie, Birmingham, AL (US)

(73) Assignees: The UAB Research Foundation, Birmingham, AL (US); Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 1412 days.

(21) Appl. No.: 15/756,937

(22) PCT Filed: Sep. 6, 2016

(86) PCT No.: PCT/US2016/050428
§ 371 (c)(1),
(2) Date: Mar. 1, 2018

(87) PCT Pub. No.: WO2017/041106
PCT Pub. Date: Mar. 9, 2017

(65) Prior Publication Data
US 2018/0250337 A1 Sep. 6, 2018

Related U.S. Application Data

(60) Provisional application No. 62/214,071, filed on Sep. 3, 2015.

(51) Int. Cl.
*A61K 35/17* (2015.01)
*A61K 31/495* (2006.01)
*A61K 39/00* (2006.01)
*A61K 45/06* (2006.01)
*A61P 35/00* (2006.01)
*C07K 14/715* (2006.01)
*C07K 14/725* (2006.01)
*C07K 16/30* (2006.01)
*C12N 5/0783* (2010.01)
*C12N 9/12* (2006.01)

(52) U.S. Cl.
CPC ............ *A61K 35/17* (2013.01); *A61K 31/495* (2013.01); *A61K 39/0011* (2013.01); *A61K 39/001104* (2018.08); *A61K 39/001106* (2018.08); *A61K 39/001109* (2018.08); *A61K 39/00111* (2018.08); *A61K 39/001112* (2018.08); *A61K 39/001113* (2018.08); *A61K 39/001119* (2018.08); *A61K 39/001122* (2018.08); *A61K 39/001124* (2018.08); *A61K 39/001126* (2018.08); *A61K 39/001129* (2018.08); *A61K 39/00115* (2018.08); *A61K 39/001151* (2018.08); *A61K 39/001164* (2018.08); *A61K 39/001166* (2018.08); *A61K 39/001168* (2018.08); *A61K 39/001171* (2018.08); *A61K 39/001174* (2018.08); *A61K 39/001181* (2018.08); *A61K 39/001182* (2018.08); *A61K 39/001188* (2018.08); *A61K 39/001189* (2018.08); *A61K 39/00119* (2018.08); *A61K 39/001193* (2018.08); *A61K 39/001195* (2018.08); *A61K 45/06* (2013.01); *A61P 35/00* (2018.01); *C07K 14/7051* (2013.01); *C07K 14/7155* (2013.01); *C07K 16/30* (2013.01); *C12N 5/0636* (2013.01); *C12N 5/0638* (2013.01); *C12N 5/0646* (2013.01); *C12N 9/12* (2013.01); *C12Y 207/10001* (2013.01); *A61K 2039/5156* (2013.01); *A61K 2039/5158* (2013.01); *A61K 2300/00* (2013.01); *C07K 2319/70* (2013.01); *C12N 2501/72* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,071,512 A | 6/2000 | Kreigler | |
| 7,078,034 B2 | 7/2006 | Lamb | |
| 10,881,688 B2 | 1/2021 | Leek et al. | |
| 11,421,005 B2 | 8/2022 | Lamb et al. | |
| 2012/0258531 A1 | 10/2012 | Spencer et al. | |
| 2012/0258532 A1 | 10/2012 | Spencer et al. | |

(Continued)

FOREIGN PATENT DOCUMENTS

| CN | 102988959 A | 3/2012 |
|---|---|---|
| CN | 104427999 A | 3/2015 |

(Continued)

OTHER PUBLICATIONS

Hombach, A. et al., 2001, J. Immunol., vol. 167: pp. 6123-6131.*

(Continued)

*Primary Examiner* — Michael D Burkhart
(74) *Attorney, Agent, or Firm* — Klarquist Sparkman, LLP; Susan Alpert Siegel

(57) ABSTRACT

The present disclosure provides novel cell compositions engineered to express at least a chimeric antigen receptor and a survival factor. Methods of using such cell compositions are also described.

30 Claims, 11 Drawing Sheets

(56) References Cited

U.S. PATENT DOCUMENTS

| | | |
|---|---|---|
| 2013/0216509 A1 | 8/2013 | Campana et al. |
| 2016/0024175 A1 | 1/2016 | Chow et al. |
| 2016/0175358 A1 | 6/2016 | Jakobovits et al. |
| 2022/0378827 A1 | 12/2022 | Spencer et al. |

FOREIGN PATENT DOCUMENTS

| | | |
|---|---|---|
| WO | WO 1997/32025 | 9/1997 |
| WO | WO 2005/097160 A2 | 10/2005 |
| WO | WO 2011/053750 | 5/2011 |
| WO | WO 2013/174404 A1 | 11/2013 |
| WO | WO 2014/164554 A1 | 10/2014 |
| WO | WO 2015/075195 A1 | 5/2015 |
| WO | WO 2015/120363 A1 | 8/2015 |
| WO | WO 2016/166544 A1 | 10/2016 |
| WO | WO2020/210774 A1 | 10/2020 |
| WO | WO2022/159582 A2 | 7/2022 |

OTHER PUBLICATIONS

International Search Report from the parent PCT Application No. PCT/US2016/050428, 4 pages, (dated Jan. 19, 2017).
Written Opinion from the parent PCT Application No. PCT/US2016/050428, 8 pages, (dated Jan. 19, 2017).
Database Accession No. EMB-623508665, Sengupta et al., "Concurrent chemotherapy and temozolomide-resistant CAR-T immunotherapy enhances glioblastoma clearance in experimental animals," *EMBASE* 2 pages (Jul. 1, 2018).
Krebs et al., "Genetically modified T cells to target glioblastoma," *Frontiers in Oncology* 3(322): 1-8 (Dec. 2013).
Migliorini et al., "Car T-Cell therapies in glioblastoma: a first look," *Clinical Cancer Research* 24(3): 535-540 (Nov. 20, 2017).
Suryadevara et al., "Temozolomide lymphodepletion enhances CAR abundance and correlates with antitumor efficacy against established glioblastoma," *Oncoimmunology* 7(6): e1434464, 10 pp. (Feb. 21, 2018).
Deniger et al., "224. Targeting B-Cell Malignancies with Chimeric Antigen Receptor-Modified γδ T Cells." *Molecular Therapy* 19 (Supplemental 1): p. S87 (2011).
Themeli et al., "Generation of Tumor-Targeted Human T lymphocytes from Induced Pluripotent Stem Cells for Cancer Therapy," *Nature Biotechnology* 31(10): 928-933 (2013).
Adair et al., "Gene therapy enhances chemotherapy tolerance and efficacy in glioblastoma patients," *The Journal of Clinical Investigation* 124(9): 4082-4092 (Sep. 2014).
Bardenheuer et al., "Resistance to cytarabine and gemcitabine and in vitro selection of transduced cells after retroviral expression of cytidine deaminase in human hematopoietic progenitor cells," *Leukemia* 19(12): 2281-2288 (Dec. 2005).
Beard et al., "Efficient and stable MGMT-mediated selection of long-term repopulating stem cells in nonhuman primates," *The Journal of Clinical Investigation* 120(7): 2345-2354 (Jul. 2010).
Bryant et al., "Characterization and immunotherapeutic potential of γδ T-cells in patients with glioblastoma," *Neuro-oncology* 11(4): 357-367 (Aug. 2009).
Cesano et al., "TALL-104 cell therapy of human solid tumors implanted in immunodeficient (SCID) mice," *Anticancer Research* 18(4A): 2289-2295 (1998).
Chamberlain, "Treatment options for glioblastoma," *Neurosurgical Focus* 20(4): E2, pp. 1-9 (Apr. 2006).
Chinnasamy et al., "Lentivirus-mediated expression of mutant MGMTP140K protects human CD34+ cells against the combined toxicity of O 6-benzylguanine and 1, 3-bis (2-chloroethyl)-nitrosourea or temozolomide," *Human Gene Therapy* 15(8): 758-769 (Aug. 2004).
Dasgupta et al., "Engineered drug-resistant immunocompetent cells enhance tumor cell killing during a chemotherapy challenge," *Biochemical and Biophysical Research Communications* 391(1): 170-175 (Jan. 2010).

Dasgupta et al., "Treatment of a solid tumor using engineered drug-resistant immunocompetent cells and cytotoxic chemotherapy," *Human Gene Therapy* 23(7): 711-721 (Mar. 2012).
Dotti et al., "Review: Current status of genetic modification of T cells for cancer treatment," *Cytotherapy* 7(2): 262-272 (2005).
Engelhardt, "Molecular mechanisms involved in T cell migration across the blood-brain barrier," *Journal of Neural Transmission* 113(4): 477-485 (Apr. 2006).
Friedman et al., "Temozolomide and treatment of malignant glioma." *Clinical Cancer Research* 6(7): 2585-2597 (Jul. 2000).
Gangadharan et al., "High-level expression of porcine factor VIII from genetically modified bone marrow-derived stem cells," *Blood* 107(10): 3859-3864 (May 2006).
Geoerger et al., "Antitumor activity of a human cytotoxic T-cell line (TALL-104) in brain tumor xenografts," *Neuro-oncology* 2(2): 103-113 (Apr. 2000).
Gerull et al., "In vivo selection and chemoprotection after drug resistance gene therapy in a nonmyeloablative allogeneic transplantation setting in dogs," *Human Gene Therapy* 18(5): 451-456 (May 2007).
Gong et al., "Characterization of a human cell line (NK-92) with phenotypical and functional characteristics of activated natural killer cells," *Leukemia* 8(4): 652-658 (Apr. 1994).
Grossman et al., "Immunosuppression in patients with high-grade gliomas treated with radiation and temozolomide," *Clinical Cancer Research* 17(16):5473-5480 (Aug. 2011).
Heimberger et al., "Immunological responses in a patient with glioblastoma multiforme treated with sequential courses of temozolomide and immunotherapy: case study," *Neuro-oncology* 10(1): 98-103 (Feb. 2008).
Hermans et al., "Synergistic effect of metronomic dosing of cyclophosphamide combined with specific antitumor immunotherapy in a murine melanoma model," *Cancer Research* 63(23): 8408-8413 (Dec. 2003).
Jiang et al., "Treatment of advanced gastric cancer by chemotherapy combined with autologous cytokine-induced killer cells," *Anticancer Research* 26(3B): 2237-2242 (May 2006).
Kershaw et al., "Supernatural T cells: genetic modification of T cells for cancer therapy," *Nature Reviews Immunology* 5(12): 928-940 (Dec. 2005).
Kushman et al., "Expression of human glutathione S-transferase P1 confers resistance to benzo [a] pyrene or benzo [a] pyrene-7, 8-dihydrodiol mutagenesis, macromolecular alkylation and formation of stable N2-Gua-BPDE adducts in stably transfected V79MZ cells co-expressing hCYP1A1," *Carcinogenesis* 28(1): 207-214 (Jan. 2007).
Lamb, "γδ T cells as immune effectors against high-grade gliomas," *Immunologic Research* 45(1): 85-95 (Oct. 2009).
Lamb et al. "γδ T cells: a new frontier for immunotherapy?," *Biology of Blood and Marrow Transplantation* 11(3): 161-168 (Mar. 2005).
Lamb et al., "Engineered drug resistant γδ T cells kill glioblastoma cell lines during a chemotherapy challenge: a strategy for combining chemo-and immunotherapy," *PLoS* 8(1): e51805, 9 pages (Jan. 2013).
Larochelle et al., "In vivo selection of hematopoietic progenitor cells and temozolomide dose intensification in rhesus macaques through lentiviral transduction with a drug resistance gene," *The Journal of Clinical Investigation* 119(7): 1962-1963 (Jun. 2009).
Litterman et al., "Profound impairment of adaptive immune responses by alkylating chemotherapy," *The Journal of Immunology* 190(12): 6259-6268 (Jun. 2013).
Mattarollo et al., "Chemotherapy and zoledronate sensitize solid tumour cells to Vγ9Vδ2 T cell cytotoxicity," *Cancer Immunology, Immunotherapy* 56(8): 1285-1297 (Aug. 2007).
Maze et al., "Retroviral-mediated expression of the P140A, but not P140A/G156A, mutant form of O 6-methylguanine DNA methyltransferase protects hematopoietic cells against O 6-benzylguanine sensitization to chloroethylnitrosourea treatment," *Journal of Pharmacology and Experimental Therapeutics* 290(3): 1467-1474 (Sep. 1999).

(56) References Cited

OTHER PUBLICATIONS

McMillin et al., "Highly efficient transduction of repopulating bone marrow cells using rapidly concentrated polymer-complexed retrovirus," *Biochemical and Biophysical Research Communications* 330(3): 768-775 (May 2005).
McMillin et al., "Complete regression of large solid tumors using engineered drug-resistant hematopoietic cells and anti-CD137 immunotherapy," *Human Gene Therapy* 17(8): 798-806 (Aug. 2006).
McMillin et al., "Abstract: Regression of large solid tumors using engineered drug resistant immunocompetent cells and selective chemotherapy," *Molecular Therapy* 9: S97-S98, Abstract No. 253 (May 2004).
Milsom et al. "Reciprocal relationship between O6-methylguanine-DNA methyltransferase P140K expression level and chemoprotection of hematopoietic stem cells," *Cancer Research* 68(15): 6171-6180 (Aug. 2008).
Mitchell et al., "Immunotherapy of malignant brain tumors," *Immunological Reviews* 222(1): 70-100 (Apr. 2008).
Neff et al., "Polyclonal chemoprotection against temozolomide in a large-animal model of drug resistance gene therapy," *Blood* 105(3): 997-1002 (Feb. 2005).
Nivens et al., "Engineered resistance to camptothecin and antifolates by retroviral coexpression of tyrosyl DNA phosphodiesterase-I and thymidylate synthase." *Cancer Chemotherapy and Pharmacology* 53(2): 107-115 (Feb. 2004).
Nowak et al., "Synergy between chemotherapy and immunotherapy in the treatment of established murine solid tumors," *Cancer Research* 63(15): 4490-4496 (Aug. 2003).
Omuro et al., "Temozolomide and methotrexate for primary central nervous system lymphoma in the elderly," *Journal of Neuro-oncology* 85(2): 207-211 (Nov. 2007).
Parkhurst et al., "Characterization of genetically modified T-cell receptors that recognize the CEA: 691-699 peptide in the context of HLA-A2.1 on human colorectal cancer cells," *Clinical Cancer Research* 15(1): 169-180 (Jan. 2009).
Pollok et al., "In vivo selection of human hematopoietic cells in a xenograft model using combined pharmacologic and genetic manipulations," *Human Gene Therapy* 14(18): 1703-1714 (Dec. 2003).
Porter et al., "Interfering RNA-mediated purine analog resistance for in vitro and in vivo cell selection," *Blood* 112(12): 4466-4474 (Dec. 2008).
Ramakrishnan et al., "Combined modality immunotherapy and chemotherapy: a new perspective," *Cancer Immunology, Immunotherapy* 57(10): 1523-1529 (Oct. 2008).
Rosenberg et al., "Cancer regression in patients with metastatic melanoma after the transfer of autologous antitumor lymphocytes," *Proceedings of the National Academy of Sciences* 101(suppl 2): 14639-14645 (Oct. 2004).
Sadelain et al., "Targeting tumours with genetically enhanced T lymphocytes," *Nature Reviews Cancer* 3(1): 35-45 (Jan. 2003).
Sawai et al., "Protection and in vivo selection of hematopoietic stem cells using temozolomide, O6-benzylguanine, and an alkyltransferase-expressing retroviral vector," *Molecular Therapy* 3(1): 78-87 (Jan. 2001).
Schroeder et al., "Abstract: Forced Expression of the "IY" Mutant Inosine Monophosphate Dehydrogenase II Results in Physiologically Significant Resistance to Mycophenolic Acid In Vitro" *Blood* (American Society of Hematology Annual Meeting Abstracts) 108: Abstract 5480 (2006).
Spencer et al., "A gene transfer strategy for making bone marrow cells resistant to trimetrexate," *Blood* 87(6): 2579-2587 (Mar. 1996).
Sugimoto et al., "Drug-selected co-expression of P-glycoprotein and gp91 in vivo from an MDR1-bicistronic retrovirus vector Ha-MDR-IRES-gp91," *The Journal of Gene Medicine* 5(5): 366-376 (May 2003).
Suzuki et al., "Enhancing effect of tumor necrosis factor (TNF)-α, but not IFN-γ, on the tumor-specific cytotoxicity of γδT cells from glioblastoma patients," *Cancer Letters* 140(1): 161-167 (1999).
Sweeney et al., "Methotrexate exacerbates tumor progression in a murine model of chronic myeloid leukemia," *Journal of Pharmacology and Experimental Therapeutics* 300(3): 1075-1084 (Mar. 2002).
Takebe et al., "Generation of dual resistance to 4-hydroperoxycyclophosphamide and methotrexate by retroviral transfer of the human aldehyde dehydrogenase class 1 gene and a mutated dihydrofolate reductase gene," *Molecular Therapy* 3(1): 88-96 (Jan. 2001).
Tam et al., "Immunotherapy of malignant melanoma in a SCID mouse model using the highly cytotoxic natural killer cell line NK-92," *Journal of Hematotherapy* 8(3): 281-290 (Jun. 1999).
Van Tellingen et al., "Overcoming the blood-brain tumor barrier for effective glioblastoma treatment," *Drug Resistance Updates* 19: 1-12 (Mar. 2015).
Yan et al., "Antileukemia activity of a natural killer cell line against human leukemias." *Clinical Cancer Research* 4(11): 2859-2868 (Nov. 1998).
Zielske et al., "In vivo selection of MGMT (P140K) lentivirus-transduced human NOD/SCID repopulating cells without pretransplant irradiation conditioning," *The Journal of Clinical Investigation* 112(10): 1561-1570 (Nov. 2003).
U.S. Appl. No. 10/881,688 B2 filed May 10, 2018, Leek et al.
Agarwala and Kirkwood, "Temozolomide, a novel alkylating agent with activity in the central nervous system, may improve the treatment of advanced metastatic melanoma," *The Oncologist* 5:144-151 (2000).
Bridgeman et al., "The optimal antigen response of chimeric antigen receptors harboring the CD3z transmembrane domain is dependent upon incorporation of the receptor into the endogenous TCR/CD3 complex," *Journal of Immunology* 184:6938-6949 (e-Pub May 17, 2010).
Chmielewski et al., "CD28 cosignalling does not affect the activation threshold in a chimeric antigen receptor-redirected T-cell attack," *Gene Therapy* 18: 62-72 (e-Pub Oct. 14, 2010).
Dotti et al., "Fifteen years of gene therapy based on chimeric antigen receptors: Are we nearly there yet?" *Human Gene Therapy* 20: 1229-1239 (Nov. 2009).
Finney et al., "Chimeric receptors providing both primary and costimulatory signaling in T cells from a single gene product," *Journal of Immunology* 161: 2791-2797 (1998).
Hudecek et al., "Receptor affinity and extracellular domain modifications affect tumor recognition by ROR1-specific chimeric antigen receptor T cells," *Clinical Cancer Research* 19(12): 3153-3164 (Jun. 15, 2013).
Park and Brentjens, "Are all chimeric antigen receptors created equal?," Journal of Clinical Oncology 33(6): 651-653 (Feb. 20, 2015).
"Racing CARs Against Cancers," https://sitn.hms.harvard.edu/flash/2013/racing-cars-against-cancer/ *Harvard University Blog* (Apr. 15, 2013).
Sengupta et al., "Abstract 2543: Concurrent chemotherapy and temozolomide-resistant CAR-T immunotherapy enhances glioblastoma clearance in experimental animals," *American Association for Cancer Research* (2018) 78 (13_Supplement): 2543 (Annual Meeting Abstract).
Thakkar et al., "Glioblastoma Multiforme," *American Association of Neurological Surgeons* https://www.aans.org/en/Patients/Neurosurgical-Conditions-and-Treatments/Glioblastoma-Multiforme 6 pages (PDF printed from the web Aug. 29, 2022).
Brown et al., "Adoptive transfer of autologous IL13-zetakine+ engineered T cell clones for the treatment of recurrent glioblastoma: lessons from the clinic," *Molecular Therapy* 19(S1): S136-S137 (May 1, 2011).
Brown et al., "Optimization of IL13Rα2-targeted chimeric antigen receptor T cells for improved anti-tumor efficacy against glioblastoma," *Molecular Therapy* 26(1): 31-44 (Jan. 2018).
Thaci et al., "Significance of interleukin-13 receptor alpha 2-targeted glioblastoma therapy," *Neuro-Oncology* 16(10): 1304-1312 (Apr. 10, 2014).
Yaghoubi et al., "Non-invasive detection of therapeutic cytolytic T cells with [18F]FHBG positron emission tomography in a glioma patient," *Nat Clin Pract Oncol.* 6(1): 53-58 (2009).

(56) References Cited

OTHER PUBLICATIONS

"CAR T Cells: Engineering Patients' Immune Cells to Treat Their Cancers," National Cancer Institute, printed from the web at: https://www.cancer.gov/about-cancer/treatment/research/car-t-cells, 14 pages (Mar. 10, 2022).

ClinicalTrials.gov ID: NCT02348216, "Study evaluating the safety and efficacy of KTE-C19 in adult participants with refractory aggressive non-Hodgkin lymphoma (ZUMA-1)," printed from the web at: https://clinicaltrials.gov/study/NCT02348216?tab=history&a=1, 19 pages (Record History, ver. 1: Jan. 27, 2015, last update posted Sep. 9, 2023).

ClinicalTrials.gov ID: NCT02445248 "Study of efficacy and safety of CTL019 in adult DLBCL patients (Juliet)," printed from the web at: https://clinicaltrials.gov/study/NCT02445248?tab=history&a=1, 21 pages (Record History, ver. 1: May 14, 2015, last update posted Nov. 5, 2023).

ClinicalTrials.gov ID: NCT02601313, "Study of brexucabtagene autoleucel (KTE-X19) in participants with relapsed/refractory mantle cell lymphoma (Cohort 1 and Cohort 2) (ZUMA-2)," printed from the web at: https://clinicaltrials.gov/study/NCT02601313?tab=history&a=1 14 pages, (Record History, ver. 1: Nov. 6, 2015, last update Oct. 26, 2023).

ClinicalTrials.gov ID: NCT02631044, Study evaluating the safety and pharmacokinetics of JCAR017 in B-cell non-Hodgkin lymphoma (Transcend-NHL-001) printed from the web at: https://www.clinicaltrials.gov/study/NCT02631044?tab=history&a=1, 21 pages (Record History, ver. 1: Dec. 11, 2015, last update posted Mar. 3, 2023).

ClinicalTrials.gov ID: NCT02658929, "Study of bb2121 in Multiple Myeloma," printed from the web at: https://clinicaltrials.gov/study/NCT02658929?tab=history&a=1, 13 pages (Record History, ver. 1: Jan. 15, 2016, last update posted Jan. 23, 2023).

Dotti et al., "Design and development of therapies using chimeric antigen receptor-expressing T cells," *Immunol Rev.* 257(1): 35 pages (Jan. 1, 2014).

\* cited by examiner

Figure 1: Treatment protocol for xenograft-bearing mice. In control groups, saline May be substituted for TMZ or γδ T Cells

GENETICALLY ENGINEERED DRUG RESISTANT T CELLS AND METHODS OF USING THE SAME

CROSS REFERENCE TO RELATED APPLICATION

This is a § 371 U.S. national stage of International Application No. PCT/US2016/050428, filed Sep. 6, 2016, which was published in English under PCT Article 21(2), which claims the benefit of U.S. Provisional Application No. 62/214,071, filed Sep. 3, 2015, which is incorporated by reference in its entirety.

ACKNOWLEDGMENT OF GOVERNMENT SUPPORT

This invention was made with government support under Grant No. NS057341, Grant No. CA097247 and Grant No. HL087969, all awarded by the National Institutes of Health. The government has certain rights in the invention.

BACKGROUND

Conventional treatment strategies for the treatment of cancers, while promising in many regards, are still in need of improvement. For example, despite extensive efforts, treatment therapies for high-grade primary brain tumors such as glioblastoma multiforme (GBM) have failed to significantly and consistently extend median survival beyond two years.

One area of research that is being investigated is immunotherapy. These treatments utilize the power of the patients' immune system to combat diseases such as cancer. In particular adoptive cell transfer is being explored. In many forms of adoptive cell transfer, the patient's immune cells are collected, expanded and modified for more efficient response. Chimeric antigen receptors (CARs) have been used in this regard. CARs are engineered receptors, which graft an arbitrary and defined specificity onto an immune effector cell. Typically, the CARs are used to graft the specificity of a monoclonal antibody onto a T cell. In this approach, T cells are removed from a patient or suitable donor and modified so that they express receptors specific to the particular form of cancer. The T cells, which can then recognize and kill the cancer cells, are reintroduced into the patient. Initial clinical studies of this approach have shown efficacy.

However, the use of CARs in adoptive cell transfer still suffer from several drawbacks. The present disclosure provides a new immune system cell composition that is engineered to express a CAR specific for a tumor antigen and a survival factor that provides resistance to an additional therapeutic treatment (such as a chemotherapy treatment regimen) that may be administered to the patient. The cell composition may further include a suicide gene and additional elements. Methods of using the cell compositions for the treatment of a disease are also provided. As such, the present disclosure provides new and needed solutions to the problems of treatment using immunotherapy. In certain embodiments, the cell compositions provided are γδ T cells.

DETAILED DESCRIPTION

Figure 1A:
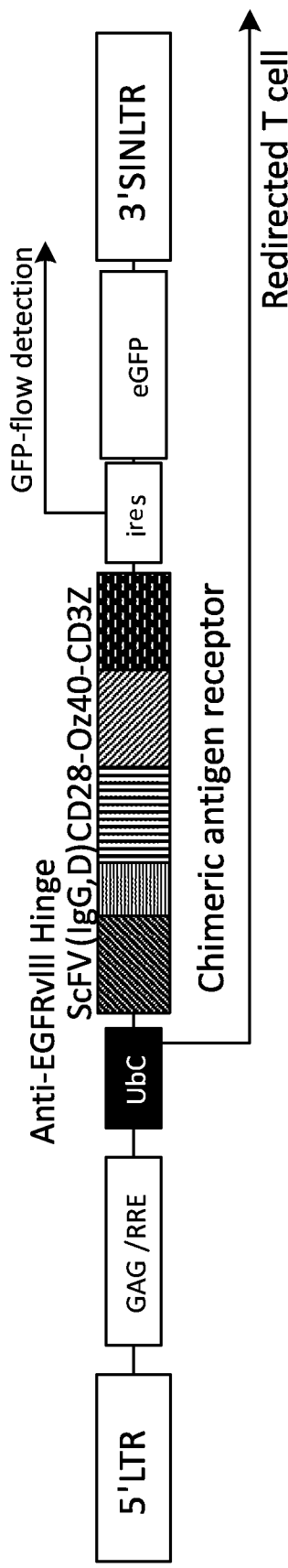
FIG. 1A shows an EGFRvIII CAR control vector co-expressing eGFP, which can be used to easily track cell transduction by flow cytometry.
Figure 1B:
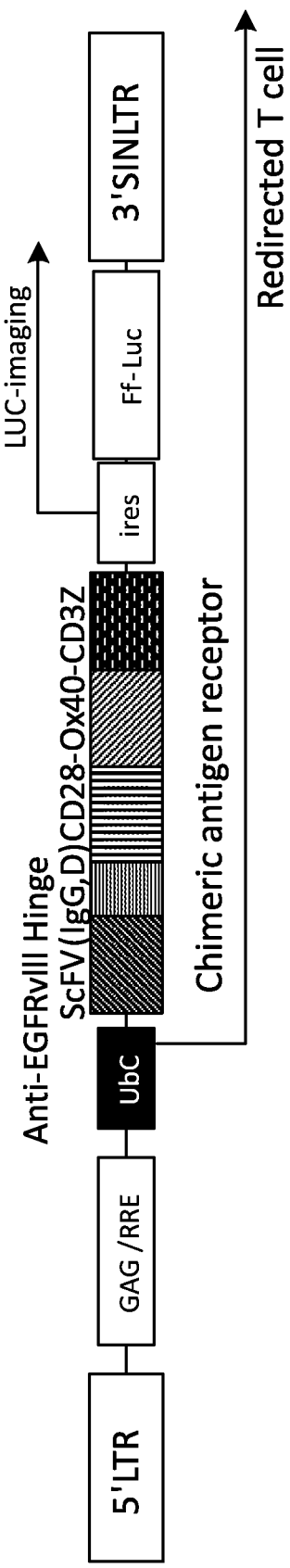
FIG. 1B shows an EGFRvIII CAR control vector co-expressing firefly luciferase, which can be used to track cell migration/homing in vivo.
Figure 1C:
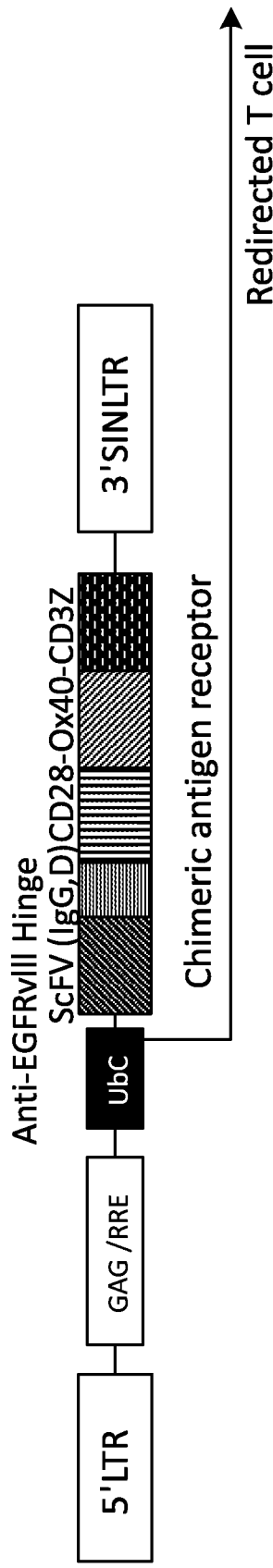
FIG. 1C shows a control vector encoding the EGFRvIII CAR, which lacks sequences coding for a survival factor and cannot confer drug resistance. The control construct can be used as a positive control for CAR expression and negative control for drug resistance.
Figure 1D:
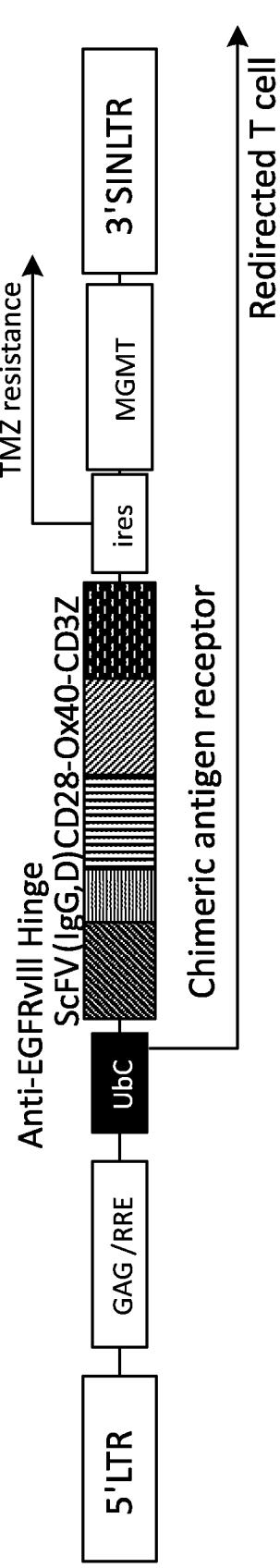
FIG. 1D shows an EGFRvIII CAR co-expressing sequences coding for a survival factor (in this figure MGMT) that confers resistance to temozolomide (TMZ). This construct is anticipated to provide the greatest benefit to in vivo treatment of glioblastoma.

Conventional treatment strategies for cancers are in need of improvement. The present disclosure provides a novel solution to the problems encountered in the art and describes novel cells compositions and methods of using the novel cell compositions for the treatment for a variety of cancers, including, but not limited to, GBM. The present disclosure provides examples of cell compositions using γδ T cells and provides specific examples of CARs and survival factors. However, other immune system cells, other CARs and other survival factors may be utilized with the present disclosure. The choice of immune system cells, CAR and survival factor may be influenced, at least in part, by the type of cancer to be treated and the additional therapies utilized in the treatment of the patient.

The present disclosure provides novel cell compositions and uses of such cell compositions in methods of treatment.

In a first aspect, the cell composition comprises an immune system cell engineered to express a CAR directed to a tumor antigen and a survival factor that allows the immune system cell to survive in a treatment environment created by an additional therapeutic treatment (for example, a polypeptide that confers resistance to a chemotherapy agent(s) that is used in conjunction with the cell compositions described).

In a second aspect, the cell composition comprises γδ T cells engineered to express a CAR directed to a tumor antigen and a survival factor that allows the γδ T cells to survive in a treatment environment created by an additional therapeutic treatment (for example, a polypeptide that confers resistance to a chemotherapy agent(s) that is used in conjunction with the cell compositions described).

In a third aspect, the cell composition comprises γδ T cells engineered to express a CAR directed to a glioma-specific tumor associated antigen (TAA) and a survival factor for resistance to temozolomide (TMZ) chemotherapy that allows the γδ T cells to survive in, for example, a TMZ chemotherapy treatment environment.

In a fourth aspect, the cell composition comprises γδ T cells engineered to express a CAR directed to the glioma-specific TAA EGFRvIII and $O^6$-Methylguanine-DNA methyltransferase (MGMT) for resistance to for example, TMZ chemotherapy that allows the γδ T cells to survive in, for example, a TMZ chemotherapy treatment environment.

In a fifth aspect, the cell composition comprises γδ T cells engineered to express a CAR directed to the glioma-specific TAA IL13Rα and MGMT for resistance to, for example, TMZ chemotherapy that allows the γδ T cells to survive in, for example, a TMZ chemotherapy treatment environment.

In a sixth aspect, the present disclosure provides a method of treating cancer comprising administering a cell composition of the present disclosure to a subject and providing an additional therapeutic treatment, before, after or both before and after, administration of the cell composition of the present disclosure.

In a seventh aspect, the present disclosure provides a method of treating glioma comprising administering a cell composition of the present disclosure to a subject and providing an additional therapeutic treatment, before, after or both before and after, administration of the cell composition of the present disclosure.

In an eight aspect, the present disclosure provides a method of treating GBM comprising administering a cell composition of the present disclosure to a subject and providing an additional therapeutic treatment, before, after or both before and after, administration of the cell composition of the present disclosure.

In a ninth aspect, the present disclosure provides a method of treating GBM comprising administering a cell composition of the fourth or fifth aspects to a subject and providing an additional therapeutic treatment, before, after or both before and after, administration of the cell composition of the present disclosure.

In a tenth aspect, the present disclosure provides a method of treating GBM comprising administering, for example, TMZ chemotherapy to a subject, administering a cell composition of the fourth or fifth aspects to a subject and optionally administering additional courses of, for example, TMZ chemotherapy and/or additional cell composition of the present disclosure.

In an eleventh aspect, the present disclosure provides a method of treating a subject suffering from cancer using an immunotherapy treatment and an additional therapeutic treatment, the method comprising: (i) administering to the subject a cell composition comprising immune system cells expressing a CAR directed to a tumor antigen, a receptor for a stress-induced antigen and a survival factor that allows the immune system cell expressing the CAR to survive in a treatment environment resulting from the additional therapeutic treatment; and (ii) administering to the subject an additional therapeutic treatment, wherein the additional therapeutic treatment is administered either before administration of the cell composition to the subject, after administration of the cell composition to the subject, concurrently with administration of the cell composition to the subject or any combination of the foregoing.

In a twelfth aspect, the present disclosure provides a method of treating a subject using an immunotherapy treatment and an additional therapeutic treatment, the method comprising: (i) administering to the subject a cell composition comprising γδ T cells expressing a CAR directed to a tumor antigen, a receptor for a stress-induced antigen and a survival factor that allows the γδ T cells expressing the CAR to survive in a treatment environment resulting from the additional therapeutic treatment; and (ii) administering to the subject an additional therapeutic treatment, wherein the additional therapeutic treatment is administered either before administration of the cell composition to the subject, after administration of the cell composition to the subject, concurrently with administration of the cell composition to the subject or any combination of the foregoing.

In a thirteenth aspect, the present disclosure provides a method of treating a subject using an immunotherapy treatment and an additional therapeutic treatment utilizing, for example, TMZ chemotherapy, the method comprising: (i) administering to the subject a cell composition comprising γδ T cells expressing a CAR directed to a glioma-specific TAA, a receptor for a stress-induced antigen and a survival factor for resistance to, for example, TMZ chemotherapy that allows the γδ T cells expressing the CAR to survive in a treatment environment resulting from the additional therapeutic treatment; and (ii) administering to the subject an additional therapeutic treatment, wherein the additional therapeutic treatment is administered either before administration of the cell composition to the subject, after administration of the cell composition to the subject, concurrently with administration of the cell composition to the subject or any combination of the foregoing.

In a fourteenth aspect, the present disclosure provides a method of treating a subject using an immunotherapy treatment and an additional therapeutic treatment utilizing, for example, TMZ chemotherapy, the method comprising: (i) administering to the subject a cell composition comprising γδ T cells expressing a CAR directed to the glioma-specific TAA EGFRvIII, a NKGD2 receptor and $O^6$-Methylguanine-DNA methyltransferase providing resistance to, for example, TMZ chemotherapy that allows the γδ T cells expressing the CAR to survive in a treatment environment resulting from the additional therapeutic treatment; and (ii) administering to the subject an additional therapeutic treatment, wherein the additional therapeutic treatment is administered either before administration of the cell composition to the subject, after administration of the cell composition to the subject, concurrently with administration of the cell composition to the subject or any combination of the foregoing.

In a fifteenth aspect, the present disclosure provides a method of treating a subject using an immunotherapy treatment and an additional therapeutic treatment utilizing, for example, TMZ chemotherapy, the method comprising: (i) administering to the subject a cell composition comprising γδ T cells expressing a CAR directed to the glioma-specific TAA IL13Rα, a NKGD2 receptor and $O^6$-Methylguanine-DNA methyltransferase providing resistance to, for example, TMZ chemotherapy that allows the γδ T cells expressing the CAR to survive in a treatment environment resulting from the additional therapeutic treatment; and (ii) administering to the subject an additional therapeutic treatment, wherein the additional therapeutic treatment is administered either before administration of the cell composition to the subject, after administration of the cell composition to the subject, concurrently with administration of the cell composition to the subject or any combination of the foregoing.

Cell Compositions

In general, the present disclosure utilizes a survival factor to provide drug resistant cellular immunotherapy (DRI). Through this mechanism, the cell compositions of the present disclosure are provided the ability to survive, expand and exert anti-tumor activity in a treatment environment after administration to the subject. The survival factor is selected based on an additional therapeutic treatment that may be used in combination with the cell compositions and methods of the present disclosure.

As used herein the phrase "survive in a treatment environment created by an additional therapeutic treatment" may be used interchangeably with the phrase, "survive in the presence of an additional therapeutic treatment" and each phrase refers to the ability of a cell to survive direct contact with an agent used in the additional therapeutic treatment or to survive in the presence of cell toxicity in the environment of the cell compositions of the invention resulting from the use of an additional therapeutic agent. Additional therapeutic treatments include, but are not limited to treatment with: anti-cancer agents, metabolic antagonists, DNA demethylating agents, plant-derived antitumor agents, a nucleoside/nucleotide-analog chemotherapy drugs, alkylating agents, antimetabolites, anticancer antibiotics, topoisomerase inhibitors, mitotic inhibitors, differentiating agents, hormone therapy agents and combinations of the foregoing. A variety of specific agents may be used in the additional therapeutic treatments as is known in the art and as discussed herein.

In one embodiment, the cell composition comprises an immune system cell engineered to express at least a CAR directed to a tumor antigen and a survival factor that allows the immune system cell to survive in a treatment environment created by an additional therapeutic treatment; for example, a polypeptide that confers resistance to a chemotherapy agent(s) that is used in conjunction with the cell compositions described. Such polypeptides that confer drug resistance to certain chemotherapeutics include, but are not limited to: MGMT, 5' nucleotidase II (NT5C2), a drug resistant variant of dihydrofolate reductase (L22Y-DHFR), thymidylate synthase, and multiple drug resistance-1 protein (MDR1).

In another embodiment, the cell composition comprises γδ T cells engineered to express at least a CAR directed to a tumor antigen and a survival factor that allows the γδ T cells to survive in a treatment environment created by an additional therapeutic treatment; (for example, a polypeptide that confers resistance to a chemotherapy agent(s) that is used in conjunction with the cell compositions described).

In another embodiment, the cell composition comprises γδ T cells engineered to express at least a CAR directed to a glioma-specific TAA and a survival factor that allows the γδ T cells to survive in a treatment environment created by an additional therapeutic treatment (for example, a polypeptide that confers resistance to a chemotherapy agent(s) that is used in conjunction with the cell compositions described).

In another embodiment, the cell composition comprises γδ T cells engineered to express at least a CAR directed to a TAA and a survival factor for resistance to, for example, TMZ chemotherapy that allows the γδ T cells to survive in a, for example, TMZ chemotherapy treatment environment.

In another embodiment, the cell composition comprises γδ T cells engineered to express at least a CAR directed to the glioma-specific TAA EGFRvIII and MGMT for resistance to, for example, TMZ chemotherapy that allows the γδ T cells to survive in a, for example, TMZ chemotherapy treatment environment.

In another embodiment, the cell composition comprises γδ T cells engineered to express at least a CAR directed to the glioma-specific TAA IL13Rα and the MGMT for resistance to, for example, TMZ chemotherapy that allows the γδ T cells to survive in a, for example, TMZ chemotherapy treatment environment.

In another embodiment, the cell composition comprises γδ T cells engineered to express at least a CAR directed to a neuroblastoma-specific TAA and a survival factor that allows the γδ T cells to survive in a treatment environment created by an additional therapeutic treatment (for example, a polypeptide that confers resistance to a chemotherapy agent(s) that is used in conjunction with the cell compositions described).

In another embodiment, the cell composition comprises γδ T cells engineered to express at least a CAR directed to a neuroblastoma-specific TAA and a survival factor for resistance to, for example, TMZ chemotherapy that allows the γδ T cells to survive in a, for example, TMZ chemotherapy treatment environment.

In another embodiment, the cell composition comprises γδ T cells engineered to express at least a CAR directed to the neuroblastoma-specific TAA GD2 and $O^6$-Methylguanine-DNA methyltransferase (MGMT) gene for resistance to, for example, TMZ chemotherapy that allows the γδ T cells to survive in a, for example, TMZ chemotherapy treatment environment.

In certain embodiments, the cell composition comprises immune system cells or γδ T cells engineered to express only a CAR directed to a tumor antigen or a glioma-specific TAA and a survival factor, such as a survival factor for resistance to, for example, TMZ. In certain embodiments, the cell composition comprises immune system cells or γδ T cells engineered to express only a CAR directed to a tumor antigen, a glioma-specific TAA or a neuroblastoma-specific TAA, a suicide gene and a survival factor, such as a survival factor for resistance to, for example, TMZ. In certain embodiments, the cell composition comprises immune system cells or γδ T cells engineered to express only a CAR directed to a tumor antigen, a glioma-specific TAA or a neuroblastoma-specific TAA, receptor for a stress-induced antigen and a survival factor, such as a survival factor for resistance to, for example, TMZ. In certain embodiments, the cell composition comprises immune system cells or γδ T cells engineered to express only a CAR directed to a tumor antigen tumor antigen, a glioma-specific TAA or a neuroblastoma-specific TAA, a receptor for a stress-induced antigen, a suicide gene and a survival factor, such as a survival factor for resistance to, for example, TMZ. In certain embodiments, the cell composition comprises immune system cells or γδ T cells engineered to express only a CAR directed to a tumor antigen, a glioma-specific TAA or a neuroblastoma-specific TAA, a NKG2D receptor and a survival factor, such as a survival factor for resistance to, for example, TMZ. In certain embodiments, the cell composition comprises immune system cells or γδ T cells engineered to express only a CAR directed to a tumor antigen, a glioma-specific TAA or a neuroblastoma-specific TAA, a NKG2D receptor, a suicide gene and a survival factor, such as a survival factor for resistance to TMZ.

In certain embodiments, the immune system cell or γδ T cell further comprises a receptor for a stress-induced antigen. In certain embodiments, the immune system cell or γδ T cell further comprises a NKGD2 receptor. In certain embodiments, the receptor for a stress-induced antigen or NKGD2 receptor is naturally present on the immune system cell or γδ T cell. In certain embodiments, the receptor for a stress-induced antigen or NKGD2 receptor is induced to an increased level on the immune system cell or γδ T cell. Therefore, in those embodiments where the cell composition comprises immune system cells or γδ T cells engineered to express only a CAR directed to a tumor antigen, a glioma-specific TAA or a neuroblastoma-specific TAA, a survival factor and optional suicide gene, the immune system cells or γδ T cells may still express a stress-induced antigen or NKGD2 receptor.

In certain embodiments, the immune system cells are any immune system cell useful in immunotherapy. In another aspect of the foregoing, the immune system cells are any cells expressing a receptor for a stress-induced antigen. In certain embodiments, the immune system cells are any cells expressing the NKG2D receptor. In certain embodiments, the immune system cells are NK cells or γδ T cells. In certain embodiments, the immune system cells are γδ T cells. In certain embodiments, the immune system cells are a combination of NK cells and γδ T cells. In certain embodiments, the immune system cells are a combination of NK cells and γδ T cells, wherein at least a portion of the NK cells and/or γδ T cells express a receptor for a stress-induced antigen. In certain embodiments, the immune system cells are a combination of NK cells and γδ T cells, wherein at least a portion of the NK cells and/or γδ T cells express a NKGD2 receptor.

In certain embodiments, the cell composition comprises a γδ T cell and an additional immune system cell. For example, the cell composition may comprises γδ T cells and a NK cells or may comprise γδ T cells, αβ T cells and a NK cells. In certain embodiments, the cell composition comprises γδ T cells and an additional immune system cell, wherein the γδ T cells are present at greater than or equal to 60% of the total cell population. In certain embodiments, the cell composition comprises γδ T cells and NK cells, wherein the γδ T cells are present at greater than or equal to 60% of the total cell population. In certain embodiments, the cell composition comprises γδ T cells and NK cells, wherein the γδ T cells are present at greater than or equal to 60% of the total cell population and the NK cells are present at less than or equal to 25%. In certain embodiments, the cell composition comprises γδ T cells and αβ T cells, wherein the γδ T cells are present at greater than or equal to 60% of the total cell population. In certain embodiments, the cell composition comprises γδ T cells and αβ T cells, wherein the γδ T cells are present at greater than or equal to 60% of the total cell population and the αβ T cells are present at less than or equal to 5%. In certain embodiments, the cell composition comprises γδ T cells, αβ T cells and NK cells, wherein the γδ T cells are present at greater than or equal to 60% of the total cell population. In certain embodiments, the cell composition comprises γδ T cells, αβ T cells and NK cells, wherein the γδ T cells are present at greater than or equal to 60% of the total cell population, the αβ T cells are present at less than or equal to 5% and the NK cells are present at less than or equal to 25%. The percentage of various cell types present, in one embodiment, is determined by flow cytometry as described in Example 3.

In certain embodiments, at least a portion of the cells comprising the cell composition (for example, the immune system cells or γδ T cells) further comprise a receptor for a stress-induced antigen. In certain embodiments, at least a portion of the cells comprising the cell composition (for example, the immune system cells or γδ T cells) further comprise a NKGD2 receptor. In certain embodiments, the receptor for a stress-induced antigen or NKGD2 receptor is naturally present on at least a portion of the cells comprising the cell composition (for example, the immune system cells or γδ T cells). In certain embodiments, the receptor for a stress-induced antigen or NKGD2 receptor is induced to an increased level at least a portion of the cells comprising the cell composition (for example, the immune system cells or γδ T cells). In certain embodiments, at least a portion of the cells comprising the cell composition (for example, the immune system cells or γδ T cells) are engineered to express the receptor for a stress-induced antigen or NKGD2 receptor. In certain embodiments, the cell composition comprises γδ T cells and at least a portion of the γδ T cells express a receptor for a stress induced antigen or a NKGD2 receptor. In certain embodiments, the cell composition comprises γδ T cells, αβ T cells and NK cells and at least a portion of the γδ T cells express a receptor for a stress induced antigen or a NKGD2 receptor. In certain embodiments, the cell composition comprises γδ T cells, αβ T cells and NK cells and at least a portion of the γδ T cells express a receptor for a stress induced antigen or a NKGD2 receptor, wherein the γδ T cells are present at greater than or equal to 60% of the total cell population. In certain embodiments, the cell composition comprises γδ T cells, αβ T cells and NK cells and at least a portion of the γδ T cells express a receptor for a stress induced antigen or a NKGD2 receptor, wherein the γδ T cells are present at greater than or equal to 60% of the total cell population, the αβ T cells are present at less than or equal to 5% and the NK cells are present at less than or equal to 25%. In certain embodiments, the receptor for a stress-induced antigen or NKGD2 receptor is naturally present on at least a portion of the γδ T cells, αβ T cells and/or NK cells. In certain embodiments, the receptor for a stress-induced antigen or NKGD2 receptor is induced to an increased level at least a portion of the γδ T cells, αβ T cells and/or NK cells. In certain embodiments, at least a portion of the γδ T cells, αβ T cells and/or NK cells are engineered to express the receptor for a stress-induced antigen or NKGD2 receptor. The percentage of various cell types present, in one embodiment, is determined by flow cytometry as described in Example 3.

In one aspect of the foregoing, the tumor antigen is any tumor antigen known in the art. In certain embodiments, the tumor antigen is selected so at least one of the following characteristics is present: the antigen is expressed in as many stages of the cancer as possible, the antigen is expressed on the surface of the tumor, the antigen is important to the viability of the tumor cell and the antigen is not expressed on non-tumor tissue or expressed at such a level that off target effects are clinically acceptable. In certain embodiments, the tumor antigen is selected from the group consisting of EphA2, B cell maturation antigen (BCMA), B7-H3, B7-H6, CAIX, CA9, CD22, CD19, CD20, ROR1, kappa or light chain, carcinoembryonic antigen, alpha-fetoprotein, CA-125, Glypican-3, epithelial tumor antigen, melanoma-associated antigen, EGP2, EGP40, EPCAM, ERBB3, ERBB4, ErbB3/4, PAP, FAR, FBP, fetal AchR, Folate Receptor α, mutated p53, mutated ras, HER2, ERBB2, HER3, folate binding protein, HIV-1 envelope glycoprotein gp120, HIV-1 envelope glycoprotein gp41, 5T4, 8H9, GD2, CD123, CD23, CD33, CD30, CD38, CD56, c-Met, fap, mesothelin, GD3, HERV-K, IL-11Rα, IL-13Rα, CSPG4, Lewis-Y, MCSP, Muc1, Muc16, NCAM, NKG2D ligands, NY-ES0-1, PRAME, PSCA, PSCl, PSMA, EGFR, Sp17, SURVIVIN, TAG72, TEM1, TEM8, EGFRvIII, and VEGFR2.

In one aspect of the foregoing, the glioma-specific TAA is any glioma-specific TAA known in the art. In certain embodiments, the glioma-specific TAA selected so at least one of the following characteristics is present: the glioma-specific TAA is expressed in as many stages of the cancer as possible, the glioma-specific TAA is expressed on the surface of the tumor, the glioma-specific TAA is important to the viability of the tumor cell and the glioma-specific TAA is not expressed on non-tumor tissue or expressed at such a level that off target effects are clinically acceptable. In certain embodiments, the glioma-specific TAA is selected from the group consisting of NKG2D ligands, ULBP-1, ULBP-2, ULBP-3, ULBP-4, ULBP-5, ULBP-6, MIC-A, MIC-B, EGFRvIII and IL13Rα. In certain embodiments, the glioma-specific TAA is EGFRvIII. In certain embodiments, the glioma-specific TAA is IL13Rα.

In one aspect of the foregoing, the neuroblastoma-specific TAA is any glioma-specific TAA known in the art. In certain embodiments, the neuroblastoma-specific TAA selected so at least one of the following characteristics is present: the neuroblastoma-specific TAA is expressed in as many stages of the cancer as possible, the neuroblastoma-specific TAA is expressed on the surface of the tumor, the neuroblastoma-specific TAA is important to the viability of the tumor cell and the neuroblastoma-specific TAA is not expressed on non-tumor tissue or expressed at such a level that off target effects are clinically acceptable. In certain embodiments, the neuroblastoma-specific TAA is selected from the group consisting of NKG2D ligands, ULBP-1, ULBP-2, ULBP-3, ULBP-4, ULBP-5, ULBP-6, MIC-A, MIC-B, and GD2. In certain embodiments, the neuroblastoma-specific TAA is GD2.

The survival factor may be any factor known in the art that provides resistance to an additional therapeutic treatment and/or allows the cells comprising the cells compositions to survive in a treatment environment (such as a chemotherapy treatment environment). In certain embodiments, the additional therapeutic treatment is treatment with an anti-cancer agent, a metabolic antagonist, a DNA demethylating agent, a plant-derived antitumor agent, a nucleoside/nucleotide-analog chemotherapy drug, an alkylating agent, an antimetabolite, an anticancer antibiotic, a topoisomerase inhibitor, a mitotic inhibitor, a differentiating agent, a hormone therapy agent and combinations of the foregoing and the survival factor provides resistance to the additional therapeutic treatment. A variety of specific agents may be used in the additional therapeutic treatments as is known in the art and as discussed herein. Representative alkylating agents include, but are not limited to, cyclophosphamide, ifosfamide and melphalan. Representative metabolic antagonists include, but are not limited to, methotrexate (MTX), 5-fluorouracil or derivatives thereof. Representative DNA demethylating agents (also known as antimetabolites) include, but are not limited to, azacitidine. Representative nucleoside/nucleotide-analog chemotherapy drugs include, but are not limited to, a substituted nucleotide and a substituted nucleoside. Representative antitumor antibiotics include, but are not limited to, mitomycin, adriamycin and doxorubicin. Representative plant-derived antitumor agents include, but are not limited to, vincristine, vindesine, TAXOL®, paclitaxel, abraxane; cisplatin; carboplatin; etoposide; and the like. Representative anti-cancer agents include, but are not limited to, trimethotrexate (TMTX), temozolomide (TMZ), raltitrexed, S-(4-Nitrobenzyl)-6-thioinosine (NBMPR), 6-benzyguanidine (6-BG), nitrosoureas [e.g., bis-chloronitrosourea (BCNU; carmustine), lomustine (CCNU)+/−Procarbazine and Vincristine (PCV regimen), doxorubicin, fotemustine, Cytarabine, camptothecin and a therapeutic derivative of any of the foregoing. Preferably, the agents used in the additional therapeutic treatment include, TMZ, doxorubicin, melphalan, nitrosoureas and any combination thereof.

In certain embodiments, the survival factor is MGMT, multidrug resistance protein 1 (MDR1), or 5' nucleotidase II (NT5C2). Other survival factors include, for example, a drug resistant variant of dihydrofolate reductase (L22Y-DHFR) and thymidylate synthase. Preferably, the survival factor in is MGMT. However, other survival factors may be used depending on the nature of the treatment environment (i.e., what other additional therapeutic treatments are being given to the patient in combination with the cells compositions of the present disclosure).

In one aspect of the foregoing, the cells of the composition further comprise a suicide gene.

In one aspect of the foregoing the cell composition comprises greater than or equal to 60%, 70&, 80%, 90%, 95% of a single type of immune system cell. In one aspect of the foregoing the cell composition comprises greater than or equal to 60%, 70%, 80%, 90%, 95% of γδ T cells. In one aspect of the foregoing the cell composition comprises greater than or equal to 60%, γδ T cells and less than or equal to 5% αβ T cells and less than or equal to 25% NK cells. The percentage of various cell types present, in one embodiment, is determined by flow cytometry as described in Example 3.

In another aspect, of the foregoing the γδ T cells are obtained from a patient and expanded/activated ex vivo; the cells may then be reintroduced to the patient.

The cell compositions described may be referred to as DRI-CAR T cells.

The cell compositions described herein may be produced by incorporating a nucleic acid construct coding for and capable of expressing a CAR and a survival factor, as well as other elements (for example, a suicide gene and/or a receptor for a stress-induced antigen). In certain embodiments, a single nucleic acid construct codes for the CAR and the survival factor, as well as other elements (for example, a suicide gene and/or a receptor for a stress-induced antigen). In certain embodiments, separate nucleic acid constructs code for the CAR and the survival factor, as well as other elements (for example, a suicide gene and/or a receptor for a stress-induced antigen). Methods of producing such nucleic acid constructs are known in the art. Representative nucleic acid constructs coding for the CAR and/or survival factor are shown in FIGS. 1A-1D.

In certain embodiments, the nucleic acid construct encodes a CAR and a survival factor.

In the above embodiments, the CAR may comprise the domains and/or sequences described herein. In certain embodiments, the nucleic acid construct encodes for a CAR comprising an ectodomain comprising a scFv directed to the EGFRvIII antigen, a hinge region, a transmembrane region and an endodomain comprising at least one signaling domain. In certain embodiments, the nucleic acid construct encodes for a CAR comprising an ectodomain comprising a scFv directed to the IL13Rα antigen, a hinge region, a transmembrane region and an endodomain comprising at least one signaling domain. In certain embodiments, the nucleic acid construct encodes for a CAR comprising an ectodomain comprising a scFv directed to the EGFRvIII antigen, a hinge region from IgG, a transmembrane region from CD3-zeta and an endodomain comprising the CD28, Ox40 and CD32 signaling domains. In certain embodiments, the nucleic acid construct encodes for a CAR comprising an ectodomain comprising a scFv directed to the IL13Rα antigen, a hinge region from IgG, a transmembrane region from CD3-zeta and an endodomain comprising the CD28, Ox40 and CD32 signaling domains.

The nucleic acid construct may be incorporated into an expression vector prior to introduction into the host cell. Such methods are known in the art. As discussed above, a single expression vector may be used or multiple expression vectors may be used depending on the nature of the nucleic acid construct. A variety of expression vectors may be used. In certain embodiments, the expression vector is a plasmid. In certain embodiments, the expression vector is a viral vector. In certain embodiments, the expression vector is a retroviral vector. In certain embodiments, the expression vector is a lentiviral vector. The expression vector may be capable of replication inside of the immune system cell (also referred to as a host cell) or the expression vector may be integrated, in whole or in part, into the genome of the immune system cell, allowing the nucleic acid construct to be replicated along with the genome of the host cell.

The expression vectors comprise a nucleic acid construct in a form suitable for expression of the nucleic acid construct in a host cell. As such, the expression vectors contains the elements required for expression of the nucleic acid construct in the host cell. The elements required will vary depending on the nature of the host cell and the vector, as well as other factors (such as level of expression desired). For example, a vector may contain one or more regulatory sequences (such as promoter sequences, enhancer sequences and other such sequences) operably linked to the nucleic acid construct allowing for expression of the nucleic acid construct. The regulatory sequences may be cell specific, such that the nucleic acid construct is expressed only in a specific cell type, or the regulatory sequences may be constitutive, such that the nucleic acid construct is expressed in any cell type.

Chimeric Antigen Receptors

The cells comprising the cell compositions of the present disclosure incorporate one or more CARs. While specific examples of CARs are given for use in treating GBM, other CARs designed for the treatment of additional cancers may also be used. The present disclosure may utilize any CAR known in the art. Methods of producing CARs with a desired specificity for a tumor associated antigen are known in the art. The CAR allows the immune system cells of the present disclosure to recognize tumor antigens in a manner that is not MHC restricted. Furthermore, a CAR may be engineered to recognize an antigen that is not protein derived.

CARs generally have the following structure: an ectodomain comprising an antigen recognition domain, a transmembrane domain and an endodomain. In certain embodiments, a peptide linker from 1 to 15 amino acids may be present in the CAR to separate the various domains of the CAR. For example, a peptide linker may be present between the antigen recognition domain and the transmembrane domain or the transmembrane domain and the endodomain. A peptide linker may be present between all domains or only between a portion of the domains. Furthermore, when the endodomain comprises more than one element, a linker peptide may be present between some or all of the individual elements in the endodomain.

CARs may be produced initially incorporating a signal sequence (which is generally later removed during processing of the CAR). The signal peptide directs the nascent protein once expressed into the endoplasmic reticulum, which allows the CAR is to be modified (for example, glycosylated) and for insertion in the cell membrane. Any eukaryotic signal peptide sequence may be used. Generally, the signal peptide natively attached to the amino-terminal most component is used (for example, in a scFv with orientation light chain-linker-heavy chain, the native signal of the light-chain is used).

The antigen recognition domain may be any domain that recognizes a tumor antigen. In specific embodiments, the antigen recognition domain is directed to a glioma-specific TAA. In specific embodiments, the antigen recognition domain is directed to a tumor antigen. In specific embodiments, the antigen recognition domain is directed to a neuroblastoma-specific TAA. Specific antigens for recognition by the antigen recognition domain are provided above. There are many alternatives for the antigen recognition domain. An antigen recognition domain from native T-cell receptor (TCR) alpha and beta single chains has been described, as have simple ectodomains (e.g. CD4 ectodomain to recognize HIV infected cells) and more exotic ectodomains comprising recognition components such as a linked cytokine (which leads to recognition of cells bearing the cytokine receptor). In fact any moiety that binds a given target with high affinity can be used as an antigen recognition region. In a preferred embodiment, the antigen recognition region is a scFV. In certain embodiments, a linker peptide (i.e., a spacer region or hinge region) links the antigen binding domain to the transmembrane domain.

In certain embodiments, the antigen recognition domain is a scFV. A scFV refers to a fusion protein of the variable regions of the heavy ($V_H$) and light chains ($V_L$) of an immunoglobulin, connected with a short linker peptide (generally of about 10 to about 25 amino acids) to produce a $V_H$-linker-$V_L$ structure (also referred to an antigen binding domain). The linker is usually rich in glycine for flexibility, as well as serine or threonine for solubility, and can either connect the N-terminus of the $V_H$ with the C-terminus of the $V_L$, or vice versa. This scFV retains the specificity of the original immuno globulin, despite removal of the constant regions and the introduction of the linker.

In certain embodiments, the antigen recognition domain is a multivalent scFV. A multivalent scFV comprises two immunoglobulin derived antigen binding domains (such as a $V_H$-linker-$V_L$ chain) joined by an additional linker, wherein the antigen binding domain recognize different antigens or different portions of the same antigen. In certain aspects, one of the antigen binding domains recognizes an activation molecule on the target cell. In certain aspects, one of the antigen binding domains recognizes an antigen that is increased in expression on the target cell as a result of the additional therapeutic treatment (such as, but not limited to, a stress induced antigen).

In certain embodiments, the antigen recognition domain is a bivalent scFV. Such bivalent scFV may have the structure $V_{H1}$-linker$_a$-$V_{L1}$-$V_H$-linker$_b$-$V_L$-linker$_c$-$V_H$-linker$_d$-$V_L$ as an example (with the understanding that the $V_H$ and $V_L$ may be arranged in different orientations as discussed above).

The linker peptide should be flexible enough to allow the antigen binding domain to adopt conformations suitable for antigen recognition and binding. The simplest form is the hinge region from IgG1. A variety of linker peptides may be used in conjunction with the CARs described herein.

The transmembrane domain is a hydrophobic region (such as an alpha helix) that spans the membrane of the cell into which the CAR is incorporated. A transmembrane domain from any membrane embedded protein may be used. Generally, the transmembrane domain from the most membrane proximal component of the endodomain is used, such as, for example to facilitate transmission of a signal from the antigen recognition domain to the endodomain. Interestingly, using the CD3-zeta transmembrane domain may result in incorporation of the artificial TCR into the native TCR a factor that is dependent on the presence of the native CD3-zeta transmembrane charged aspartic acid residue.

The endodomain allows transmission of a signal after antigen binding. After antigen recognition, receptors cluster and a signal is transmitted to the immune system cell containing the CAR. The endodomain comprises at least one signaling domain. In certain embodiments, the endodomain comprises more than 1 signaling domain. The most commonly used signaling domain is CD3-zeta, which contains three immunoreceptor tyrosine-based activation motifs (ITAMs). Therefore, in certain embodiments the signaling domain comprises at least one ITAM. In certain embodiments, the endodomain comprises CD3-zeta. In certain embodiments, the endodomain comprises CD3-zeta and at least one additional signaling domain. The endodomain transmits an activation signal to the cell after antigen is bound. "First-generation" CARs typically have the endodomain from the CD3-zeta, which is the primary transmitter of signals from endogenous TCRs. "Second-generation" CARs add intracellular signaling domains from various costimulatory protein receptors (e.g., CD28, 41BB, DAP10, OX40 or ICOS) to the cytoplasmic tail of the endodomain to provide additional signals to the T cell. More recent, "third-generation" CARs have an endodomain that combine multiple signaling domains, such as CD3-zeta-CD28-41BB or CD3-zeta-CD28-OX40, to further augment potency. In certain embodiments, the endodomain comprises CD3-zeta-CD28-OX40.

Methods of Use

Methods of using the cell compositions of the present disclosure are also described.

In one embodiment, the present disclosure provides a method of treating cancer comprising administering a cell composition of the present disclosure to a subject and providing an additional therapeutic treatment, before, after or both before and after, administration of the cell composition of the present disclosure.

In another embodiment, the present disclosure provides a method of treating glioma comprising administering a cell composition of the present disclosure to a subject and providing an additional therapeutic treatment, before, after or both before and after, administration of the cell composition of the present disclosure.

In another embodiment, the present disclosure provides a method of treating GBM comprising administering a cell composition of the present disclosure to a subject and providing an additional therapeutic treatment, before, after or both before and after, administration of the cell composition of the present disclosure.

In another embodiment, the present disclosure provides a method of treating GBM comprising administering a cell composition comprising γδ T cells engineered to express a CAR directed to the glioma-specific TAA EGFRvIII or IL13Rα and the MGMT gene for resistance to, for example, TMZ chemotherapy to a subject and providing an additional therapeutic treatment, before, after or both before and after, administration of the cell composition of the present disclosure.

In another embodiment, the present disclosure provides a method of treating GBM comprising administering, for example, TMZ chemotherapy to a subject, administering a cell composition comprising γδ T cells engineered to express a CAR directed to the glioma-specific TAA EGFRvIII or IL13Rα and the MGMT gene for resistance to, for example, TMZ chemotherapy and optionally administering additional courses of, for example, TMZ chemotherapy and/or additional cell composition of the present disclosure.

In another embodiment, the present disclosure provides a method of treating a subject suffering from cancer using an immunotherapy treatment and an additional therapeutic treatment, the method comprising: (i) administering to the subject a cell composition comprising immune system cells expressing a CAR directed to a tumor antigen, a receptor for a stress-induced antigen and a survival factor that allows the immune system cell expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In another embodiment, the present disclosure provides a method of treating a subject suffering from cancer using an immunotherapy treatment and an additional therapeutic treatment, the method comprising: (i) administering to the subject a cell composition comprising γδ T cells expressing a CAR directed to a tumor antigen, a receptor for a stress-induced antigen and a survival factor that allows the γδ T cells expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In another embodiment, the present disclosure provides a method of treating a subject suffering from glioma using an immunotherapy treatment and an additional therapeutic treatment utilizing TMZ or other appropriate chemotherapy, the method comprising: (i) administering to the subject a cell composition comprising γδ T cells expressing a CAR directed to a glioma-specific TAA, a receptor for a stress-induced antigen and a survival factor for resistance to, for example, TMZ chemotherapy that allows the γδ T cells expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In another embodiment, the present disclosure provides a method of treating a subject suffering from neuroblastoma using an immunotherapy treatment and an additional therapeutic treatment utilizing, for example, TMZ chemotherapy, the method comprising: (i) administering to the subject a cell composition comprising γδ T cells expressing a CAR directed to a neuroblastoma-specific TAA, a receptor for a stress-induced antigen and a survival factor for resistance to, for example, TMZ chemotherapy that allows the γδ T cells expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In another embodiment, the present disclosure provides a method of treating a subject suffering from glioma an immunotherapy treatment and an additional therapeutic treatment utilizing, for example, TMZ chemotherapy, the method comprising: (i) administering to the subject a cell composition comprising γδ T cells expressing a CAR directed to the glioma-specific TAA EGFRvIII, a NKGD2 receptor and $O^6$-Methylguanine-DNA methyltransferase providing resistance to, for example, TMZ chemotherapy that allows the γδ T cells expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In another embodiment, the present disclosure provides a method of treating a subject suffering from cancer using an immunotherapy treatment and an additional therapeutic treatment utilizing, for example, TMZ chemotherapy, the method comprising: (i) administering to the subject a cell composition comprising γδ T cells expressing a CAR directed to the glioma-specific TAA IL13Rα, a NKGD2 receptor and $O^6$-Methylguanine-DNA methyltransferase providing resistance to, for example, TMZ chemotherapy that allows the γδ T cells expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In another embodiment, the present disclosure provides a method of treating a subject suffering from neuroblastoma using an immunotherapy treatment and an additional therapeutic treatment utilizing, for example, TMZ chemotherapy, the method comprising: (i) administering to the subject a cell composition comprising γδ T cells expressing a CAR directed to the neuroblastoma-specific TAA GD2, a NKGD2 receptor and $O^6$-Methylguanine-DNA methyltransferase providing resistance to, for example, TMZ chemotherapy that allows the γδ T cells expressing the CAR to survive in a treatment environment resulting from the additional therapeutic treatment; and (ii) administering to the subject the additional therapeutic treatment, wherein the additional therapeutic treatment is administered either before administration of the cell composition to the subject, after administration of the cell composition to the subject, concurrently with administration of the cell composition to the subject or any combination of the foregoing.

In certain embodiments of any of the foregoing methods, the cell composition is any cell composition described herein. In certain embodiments of any of the foregoing methods, the cell composition may be administered to the subject more than one time, with the additional therapeutic treatment being administered either before, after or both before and after each administration of the cell composition. In certain embodiments of any of the foregoing methods, the cell composition may be administered to the subject more than one time, with the additional therapeutic treatment being administered either before, after or both before and after the first administration of the cell composition and optionally either before, after or both before and after each additional administration of the cell composition. In certain embodiments of any of the foregoing methods, the cell composition may be administered to the subject one time per week for 2 weeks, three weeks or 4 weeks or greater.

In certain embodiments of any of the foregoing methods, the additional therapeutic treatment is administered to the subject from 24 to 48 hours before, after or both before or after administration of the cell composition. In certain embodiments of any of the foregoing methods, the cell composition is administered to the subject on day X and the additional therapeutic treatment is administered to the subject 12 to 72 hours prior to day X, 12 to 72 hours after day X or both 12 to 72 hours prior to and after day X. In certain embodiments of any of the foregoing methods, the cell composition is administered to the subject on day X and the additional therapeutic treatment is administered to the subject 12 to 72 hours prior to day X, 12 to 72 hours after day X or both 12 to 72 hours prior to and after day X, followed by an additional administration of the cell composition to the subject on day Y, with optional administration of the additional therapeutic treatment to the subject 12 to 72 hours prior to day Y, 12 to 72 hours after day Y or both 12 to 72 hours prior to and after day Y.

In one aspect of any of the foregoing methods, the CAR of the cell composition is specific for the cancer to be treated. In one aspect of any of the foregoing methods, the survival factor of the cell composition confers resistance to the therapeutic treatment/additional therapeutic treatment.

The cell compositions of the present disclosure may be administered by any method known in the art. In one aspect of any of the foregoing methods, the cell composition is administered intravenously. In one aspect of any of the foregoing methods, the cell composition is administered intra-cranially. In one aspect of any of the foregoing methods, the cell composition is administered intra-arterially. In one aspect of any of the foregoing methods, the cell composition is administered directly into the tumor bed. In one aspect of any of the foregoing methods, the cell composition is administered near or adjacent to the tumor. In one aspect of any of the foregoing Methods, the cell composition is administered by a combination of the foregoing.

In one aspect of any of the foregoing methods, the additional therapeutic treatment (for example TMZ chemotherapy) provides at least one the following benefits: increased effectiveness of the cell composition through induction of stress-induced antigens, increased homeostatic reconstitution of the cell composition, increased in vivo proliferation, and increased persistence of the cell composition (the foregoing compared to a similar treatment when the additional therapeutic treatment is omitted).

In certain embodiments, the cancer is sensitive to the additional therapeutic treatment for which the cells are engineered to be resistant. Such additional therapeutic treatment to which cancer cells may be sensitive to include, but are not limited to: anti-cancer agents, metabolic antagonists, DNA demethylating agents, plant-derived antitumor agents, a nucleoside/nucleotide-analog chemotherapy drugs, alkylating agents, antimetabolites, anticancer antibiotics, topoisomerase inhibitors, mitotic inhibitors, differentiating agents, hormone therapy agents and combinations of the foregoing. A variety of specific agents may be used in the additional therapeutic treatments as is known in the art and as discussed herein. Representative alkylating agents include, but are not limited to, cyclophosphamide, ifosfamide and melphalan. Representative metabolic antagonists include, but are not limited to, methotrexate (MTX), 5-fluorouracil or derivatives thereof. Representative DNA demethylating agents (also known as antimetabolites) include, but are not limited to, azacitidine. Representative nucleoside/nucleotide-analog chemotherapy drugs include, but are not limited to, a substituted nucleotide and a substituted nucleoside. Representative antitumor antibiotics include, but are not limited to, mitomycin, adriamycin and doxorubicin. Representative plant-derived antitumor agents include, but are not limited to, vincristine, vindesine, TAXOL®, paclitaxel, abraxane; cisplatin; carboplatin; etoposide; and the like. Representative anti-cancer agents include, but are not limited to, trimethotrexate (TMTX), temozolomide (TMZ), raltitrexed, S-(4-Nitrobenzyl)-6-thioinosine (NBMPR), 6-benzyguanidine (6-BG), nitrosoureas [e.g., bis-chloronitrosourea (BCNU; carmustine), lomustine (CCNU)+/−Procarbazine and Vincristine (PCV regimen), doxorubicin, fotemustine, Cytarabine, camptothecin and a therapeutic derivative of any of the foregoing. Preferably, the agents used in the additional therapeutic treatment to which cancer cells may be sensitive to include, TMZ, doxorubicin, melphalan, nitrosoureas and any combination thereof.

In certain embodiments, the cancer is resistant to the additional therapeutic treatment for which the cells are engineered to be resistant. In such embodiments, the additional therapeutic treatment provides for at least one of the benefits described above. In one embodiment, the additional therapeutic treatment increase the expression of a stress-induced antigen, which are ligands for the NKG2D receptor. Specific stress-induced antigens that are upregulated include, but are not limited to, ULBP-1, ULBP-2, ULBP-3, ULBP-4, ULBP-5, ULBP-6, MIC-A and MIC-B.

In certain embodiments, the cancer is selected from the group consisting of: brain cancer, breast cancer, prostate cancer, lung cancer, colon cancer, epithelial cancer, head and neck cancer, skin cancer, cancers of the genito-urinary tract, ovarian cancer, endometrial cancer, cervical cancer, kidney cancer, gastric cancer, cancer of the small intestine, liver cancer, pancreatic cancer, gall bladder cancer, cancers of the bile duct, esophageal cancer, cancer of the salivatory glands, thyroid cancer, and hematological malignancies, leukemia, lymphoma, multiple myeloma, and myelodysplastic syndromes.

In certain embodiments, the cancer is brain cancer. In certain embodiments, the cancer is pineal tumors, pituitary tumors, PNET, schwannoma, lymphoma, medulloblastoma, meningioma, metastatic brain cancer, neurofibroma, neuronal & mixed neuronal-glial tumors, oligoastrocytoma, oligodendroglioma, astrocytoma, atypical teratoid rhaboid tumor (ATRT), chondrosarcoma, choroid plexus tumors, craniopharyngioma, ependymoma, germ cell tumor, neuroblastoma, glioblastoma (GBM) and glioma. In certain embodiments, the cancer is glioblastoma. In certain embodiments, the cancer is neuroblastoma.

In certain embodiments, the tumor antigen is any tumor antigen known in the art. In certain embodiments, the tumor antigen is selected so at least one of the following characteristics is present: the antigen is expressed in as many stages of the cancer as possible, the antigen is expressed on the surface of the tumor, the antigen is important to the viability of the tumor cell and the antigen is not expressed on non-tumor tissue or expressed at such a level that off target effects are clinically acceptable. In certain embodiments, the tumor antigen is selected from the group consisting of EphA2, B cell maturation antigen (BCMA), B7-H3, B7-H6, CAIX, CA9, CD22, CD19, CD20, ROR1, kappa or light chain, carcinoembryonic antigen, alpha-fetoprotein, CA-125, Glypican-3, epithelial tumor antigen, melanoma-associated antigen, EGP2, EGP40, EPCAM, ERBB3, ERBB4, ErbB3/4, PAP, FAR, FBP, fetal AchR, Folate Receptor α, mutated p53, mutated ras, HER2, ERBB2, HER3, folate binding protein, HIV-1 envelope glycoprotein gp120, HIV-1 envelope glycoprotein gp41, 5T4, 8H9, GD2, CD123, CD23, CD33, CD30, CD38, CD56, c-Met, fap, mesothelin, GD3, HERV-K, IL-11Rα, IL-13Rα, CSPG4, Lewis-Y, MCSP, Muc1, Muc16, NCAM, NKG2D ligands, NY-ES0-1, PRAME, PSCA, PSCl, PSMA, EGFR, Sp17, SURVIVIN, TAG72, TEM1, TEM8, EGFRvIII, and VEGFR2.

In certain embodiments, the glioma-specific TAA is any glioma-specific TAA known in the art. In certain embodiments, the glioma-specific TAA selected so at least one of the following characteristics is present: the glioma-specific TAA is expressed in as many stages of the cancer as possible, the glioma-specific TAA is expressed on the surface of the tumor, the glioma-specific TAA is important to the viability of the tumor cell and the glioma-specific TAA is not expressed on non-tumor tissue or expressed at such a level that off target effects are clinically acceptable. In certain embodiments, the glioma-specific TAA is selected from the group consisting of NKG2D ligands, ULBP-1, ULBP-2, ULBP-3, ULBP-4, ULBP-5, ULBP-6, MIC-A, MIC-B, GD2, EGFRvIII and IL13Rα. In certain embodiments, the glioma-specific TAA is EGFRvIII. In certain embodiments, the glioma-specific TAA is IL13Rα.

In certain embodiments, the neuroblastoma-specific TAA is any glioma-specific TAA known in the art. In certain embodiments, the neuroblastoma-specific TAA selected so at least one of the following characteristics is present: the neuroblastoma-specific TAA is expressed in as many stages of the cancer as possible, the neuroblastoma-specific TAA is expressed on the surface of the tumor, the neuroblastoma-specific TAA is important to the viability of the tumor cell and the neuroblastoma-specific TAA is not expressed on non-tumor tissue or expressed at such a level that off target effects are clinically acceptable. In certain embodiments, the neuroblastoma-specific TAA is selected from the group consisting of NKG2D ligands, ULBP-1, ULBP-2, ULBP-3, ULBP-4, ULBP-5, ULBP-6, MIC-A, MIC-B, and GD2. In certain embodiments, the neuroblastoma-specific TAA is GD2.

DRI genetic engineering, for example the use of the MGMT gene, enables the cell compositions of the present disclosure to function in a chemotherapy-rich environment at a time when the tumor is likely to be maximally stressed.

The stress effect on the tumor in certain embodiments increases the expression of stress antigens, which are recognized by receptors, such as the NKG2D receptor, on γδ T cells. The dual effect of inducing stress antigens and decreasing regulatory T cells with chemotherapy significantly improve tumor reduction over either individual regimen. Gene modification protects the cell compositions of the present disclosure from the lympho depleting effects of a chemotherapy regimen, for example TMZ, and allows the cell compositions of the present disclosure specific access to the tumor via TAA combined with unimpaired T cell cytotoxic function at the time that malignant cells are maximally stressed by chemotherapy. The use of the cell compositions of the present disclosure (referred to as DRI-CAR T cell therapy) is believed to significantly prolong survival and reduce tumor burden when compared with either chemotherapy (for example, TMZ) treatment alone or γδ T cell infusion alone and do so without significant adverse systemic or neurologic consequences.

The rationale for the cell compositions and methods of the present disclosure is based on previous work showing (a) human GBM cells are highly vulnerable to attack by ex vivo expanded/activated γδ T cells (1, 2) (b) local intracranial injection of expanded/activated γδ T cells extends survival of tumor-bearing mice by slowing and slows progression of GBM xenografts (3) and GL261-derived tumors in an immunocompetent C56BL/6 mouse model; (c) TMZ-resistant clones of the human SNB-19 and U373 GBM cell lines are killed with significantly greater efficacy by MGMT-modified γδ T cells in the presence of TMZ than by either TMZ or γδ T cells (4) and, most importantly, (d) mice bearing either unmodified or TMZ-resistant clones of primary human GBM xenografts show improved survival when treated with intracranial injections of gene-modified γδ T cells when compared to either treatment alone. Therefore, cell compositions of the present disclosure comprising γδ T cells modified for resistance to an additional therapeutic treatment (for example, TMZ), are expected to significantly prolong survival and reduce tumor burden when compared with either separate treatment and will do so without causing significant adverse systemic or neurologic consequences.

Several recent studies have shown strategic timing of chemotherapy and immunotherapy for solid extra-cranial neoplasms leverages the innate response to chemotherapy-induced expression of stress-associated antigens on tumor cells (8-10) and depletion of regulatory T cells. The dual effect of inducing stress antigens and decreasing regulatory T cells can result in significantly improved tumor reduction over either individual regimen (11-17). Successful implementation of this strategy for cancers, including, but not limited to, GBM, would be a significant departure from classical approaches that have relied on adaptive recognition of tumor-associated antigens (18, 19), glioma cell MHC Class I expression (20, 21), or lymphokine-activated killer (LAK) cell therapy (22-26).

Applicants have previously developed a robust system for manufacture of expanded/activated γδ T cells that definitively target high-grade gliomas via stress-induced antigens (i.e., NKG2D ligands) expressed by the tumor (3, 27, 28). Both in vitro cytotoxicity and improved survival/increased time to progression in specific in vivo models designed to replicate therapeutic conditions have been shown (1, 2). The applicants have shown TMZ transiently upregulates expression of NKG2D ligands on the glioma cell surface and renders the tumor more vulnerable to recognition by γδ T cells (4, 8), and killing of TMZ-resistant glioma lines is enhanced by MGMT gene-modified γδ T cells in the presence of therapeutic concentrations of TMZ. Through the use of the cell compositions and methods of the present disclosure, the timing of cellular immunotherapy and chemotherapy can be adjusted to maximize the effects of both. Therefore, the present disclosure not only provides novel cell compositions as described but a novel anti-glioblastoma treatment strategy, providing a previously unexplored avenue for treatment of high-grade gliomas.

While it is possible to administer the cell composition of the present disclosure directly into the tumor bed via surgically placed catheters (for example, a ventriculostomy catheter), the time interval between resection and TMZ dose intensification may span up to eight weeks, exposing the patient to potential risk of infection or an additional procedure for catheter placement near the time of cell therapy administration. The CARs incorporated into the cell compositions described are designed to target tumor associated antigens (for example, glioma-specific tumor-associated antigens) in order to concentrate DRI-CAR T cells in the tumor when administered to patient by a variety of methods of administration allowing for a variety of methods of administration to be used. For example, when the cell composition is administered to the patient by an intravenous route or an intra-arterial route, the CARs incorporated into the cell compositions described aid in increasing infiltration of the DRI-CAR T cells into the tumor bed and allow increased concentrations of the DRI-CAR T cells in the tumor bed. Likewise, when administered other means (for example, via a Rickham catheter or similar device directly into the tumor bed or by intra-ventricular administration) the CARs incorporated into the cell compositions described allow the same result to be achieved. Activation and cytotoxicity can be mediated via the CAR and/or by recognition of NKG2D ligands by γδ T cells, a particularly important strategy in a heterogeneous tumor that does not express TAA in sufficient density to activate T cells via the CAR. Importantly, this therapy takes place during high-dose chemotherapy when tumor cells are highly stressed; regulatory T cells are depleted, other tumor-associated immune defenses compromised, and the vascular bed more permeable. TMZ-mediated lymphodepletion also favors homeostatic reconstitution, in vivo proliferation, and persistence of the DRI-CAR T cells.

Figure 8A:
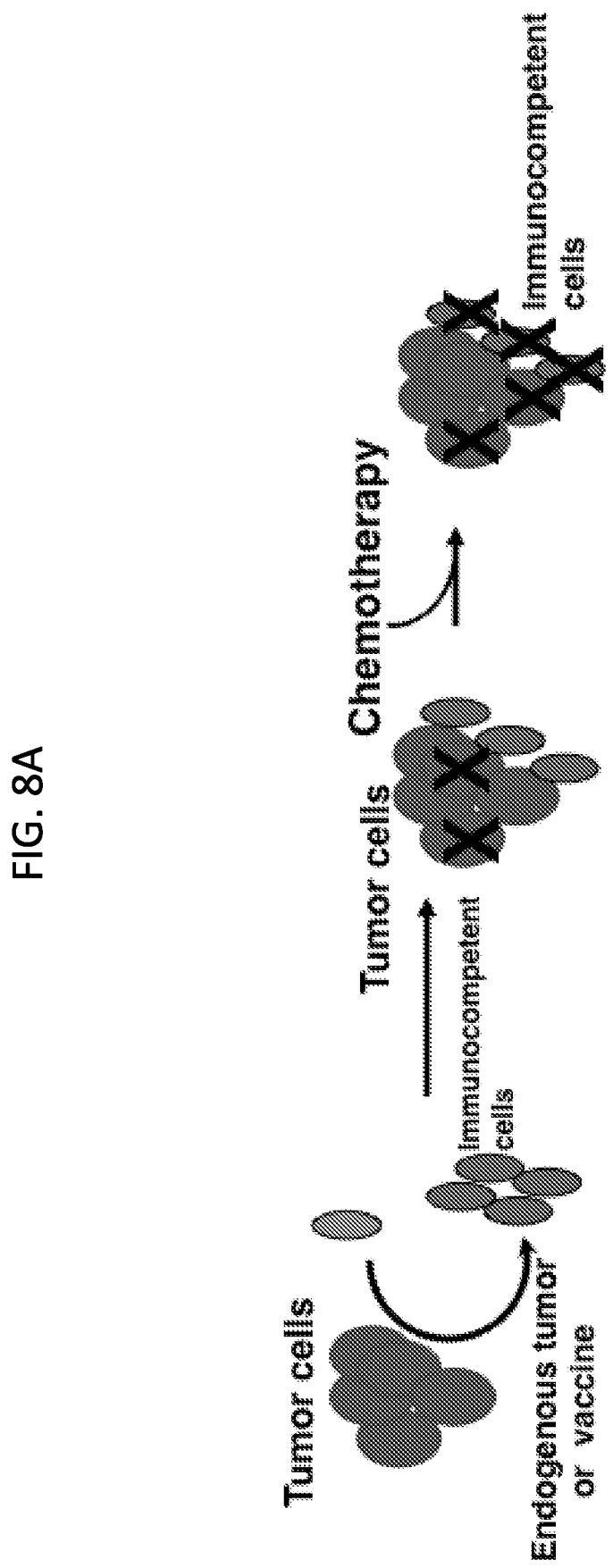
FIG. 8A shows one embodiment of the methods of the prior art.
Figure 8B:
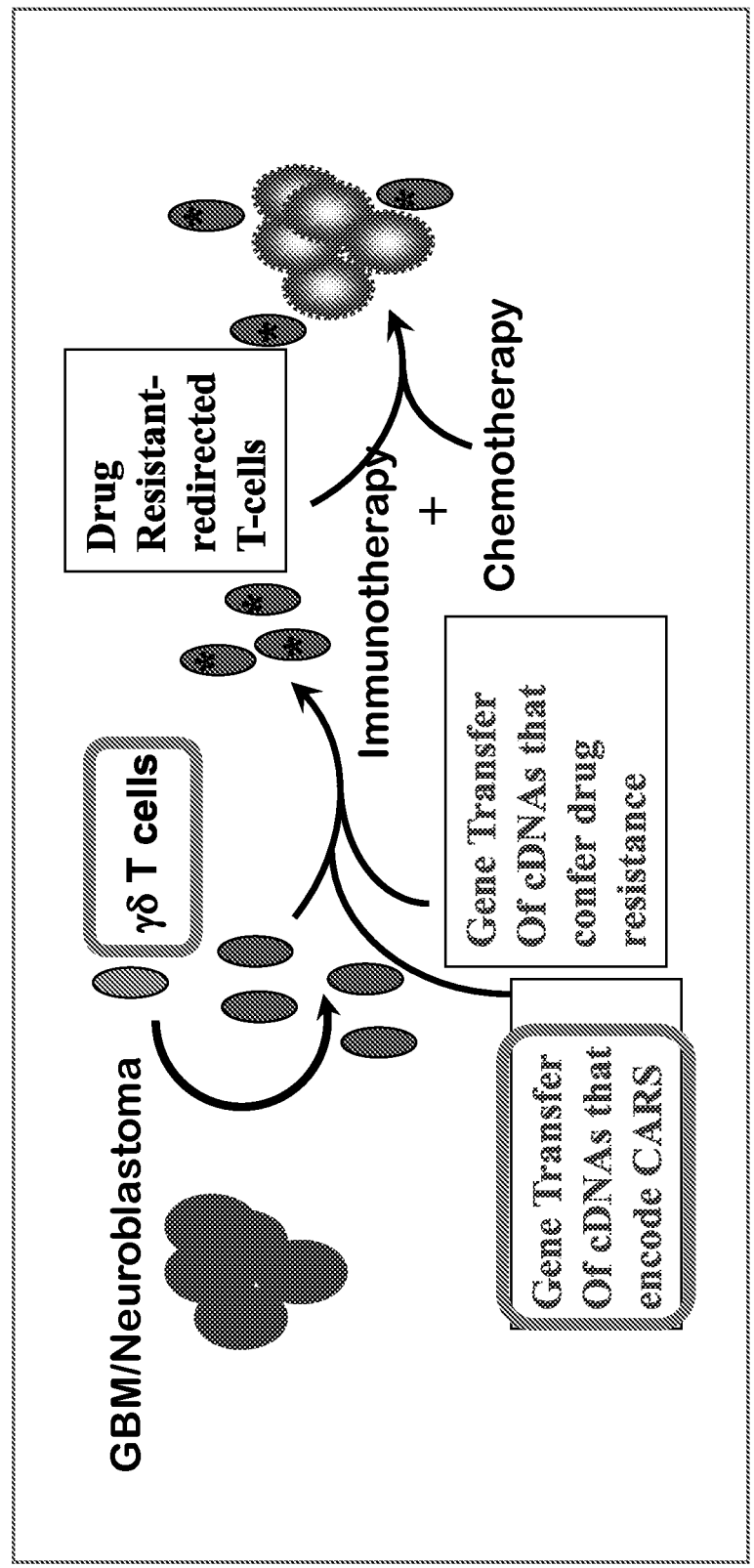
FIG. 8B shows one embodiment of the methods of the present disclosure.

A summary of the prior art methods of immunotherapy and the improved methods of the present disclosure are shown in FIGS. 8A and 8B, respectively. In the prior art methods, immunocompetent cells were generated by cytokine treatment and other methods. The immunocompetent cells as such displayed tumoricidal activity. When additional treatments were administered, for example, chemotherapy regimens, the immunocompetent cells were depleted, limiting the effectiveness of the treatment due to killing of the therapeutic cells. The methods of the present disclosure overcome such limitations by providing cells compositions, such as, but not limited to, γδ T cells, comprising a tumor specific CAR and a survival factor (DRI-CAR). When combined with additional therapeutic treatments, such as chemotherapy regimens, the DRI-CAR cells retain the ability to attack tumor cells by virtue of the CARs present as well as through recognition of stress-induced ligands while being able to survive in the treatment environment. Furthermore, the reduction of regulatory T-cells provides an additional therapeutic advantage. Still further, lymphodepletion through the chemotherapy regimen also favors homeostatic reconstitution, in vivo proliferation, and persistence of the DRI-CAR T cells, further improving therapeutic outcomes.

EXAMPLES

Example 1—Development and In Vitro Testing of Genetically Engineered γδ T Cells

Lentiviral vectors that co-express cDNA sequences for a CAR and a survival factor to confer drug resistance will be generated to determine vector configurations that provide optimal transgene expression and to determine the optimal transduction timing for producing genetically engineered γδ T cells. In order to quantify optimal delivery and persistence, engineered γδ T cells immunotherapy with $^{111}$[In]-labeled γδ T cells bearing either an EGFRvIII or IL13rα (DRI-CAR) will be evaluated by comparing potency, persistence, and efficacy of intracranial versus intravenous routes of administration against patient-derived glioma xenolines during TMZ chemotherapy in immunodeficient mice.

Vectors encoding IL13Rα and EGFRvIII CAR that recognize glioma cells and are known to target glioblastoma (GBM) will be generated. In addition, a cDNA encoding MGMT, which confers resistance to TMZ will be co-expressed with the CAR. Control vectors encoding flow or imaging markers for optimal analysis of gene transfer and tracking of genetically modified cells will also be generated. Exemplary constructs encoding a EGFRvIII CAR are shown in FIG. 1).

Previous work from the inventors has verified that the optimal transduction time for insertion of a simple SIV-encoded p140K-MGMT vector is between 3 and 7 days following initiation of Zoledronate/IL2-based γδ T cell expansion culture. Under these conditions, MGMT copy numbers sufficient to confer resistance to TMZ at concentrations exceeding 400 μM were generated with a MOI as low as 5. These conditions will be verified and optimized for DRI-CAR transductions using a matrix of transduction times and MOI spanning days 2 to 7 and MOI from 1 to 25.

TABLE 1

Experimental Design

| Group | n | Tumor | Treatment (see FIG. 2) |
|---|---|---|---|
| 1 | 20 | Yes | No treatment |
| 2 | 20 | Yes | TMZ 60 mg/kg IP |
| 3 | 20 | Yes | IV gene-modified γδ T cells, (1.5 × 10$^8$/kg), TMZ 60 mg/kg IP |
| 4 | 20 | Yes | IC gene-modified γδ T cells (1.5 × 10$^6$), TMZ 60 mg/kg IP |

Intracranial glioma xenografts will consist of parent (designated by "P") and TMZ-resistant clones (designated by "T") of the GBM-X12 (Classical), GBM-X22 (Mesenchymal), GBM-X1066 (neural), and GBM-XD456 (proneural) explants from primary GBM. Mice will be injected with either 1.5×10$^6$ cell/kg (intracranial) or 5×10$^8$ cells/kg (intravenous) $^{111}$[In]-labeled DRI-CAR γδT cells using methods developed by Beck (5) and various treatments evaluated based on the experimental design shown in Table I (IC=intra-cranial; IP=intra-peritoneal IV=intravenous) and FIG. 2. Imaging studies will be conducted at 24 h intervals for a minimum of 3 days following injection by X-SPECT as modeled for breast tumors in FIG. 3. Biodistribution studies will also be performed separately 24 h following injection of 5×10$^8$ cells/kg $^{111}$[In]-labeled γδ T cells/kg and counting of major organs and tumor with results expressed as % $^{111}$[In] injected dose (ID)/g. Tumor localization of γδT cells will be derived from the color scale associated with the image and quantitated by accumulated radioactivity within the tumor expressed (by convention) as the percent of injected radiation dose found per gram of tumor. It is expected that intravenous administration as well as intracranial administration will be effective.

The potency of each DRI-CAR product will be determined with in vitro cytotoxicity assays against the four selected xenolines. Efficacy will be evaluated by comparison of survival of tumor-bearing mice treated based on the experimental design shown in Table I and FIG. 2 with untreated controls. Tumor and normal tissues will be harvested for histologic and functional assessments including tumor histopathology, invasion, lymphocyte infiltration, and lymphocyte immunophenotype. Statistical analysis will be performed utilizing nonparametric t-tests and/or ANOVA for migration and distribution studies as well as nonparametric log-rank analysis of survival data. Projecting a difference of 0.15 between treatment and control groups, 20 replicates/group provides a power of 80% to detect differences at $p \leq 0.05$.

Example 2—Evaluation of Safety of DRI-CAR Therapy Under Conditions Likely to be Prevalent During Treatment (e.g. Prior Radiation Therapy, TMZ)

The cell compositions and methods of the present disclosure will be tested for the potential for local off-target cytotoxicity using an in vitro toxicology assay of DRI-CAR against cultured human astrocytes. Furthermore, it will be determined if γδ T cells expressing a suicide gene confers safety advantages that would be considered advantageous. Vector integration site analysis, will also be determined. In vitro toxicological analysis will be conducted as these is no comparable animal model for Vγ9Vδ2 T cells. DRI-CAR T cells (20 repetitions) will be tested against cultured human astrocytes exposed to either 250 cGy of ionizing radiation or 4 h incubation in 200 μM TMZ and compared to untreated astrocytes by assessment of NKG2D ligand expression and DRI-CAR cell-mediated cytotoxicity. Initial work reveals slight upregulation MIC-A and ULBP2 and no significant γδ T cell cytotoxicity against cultured astrocytes.

In order to protect against a cascading inflammatory response or off-target cytotoxicity, a suicide gene will be evaluated for incorporation into the CAR gene product. The γ-retrovirus, SFG.iCaspase9.2A.DeltaCD19, consists of iC9 linked, via a 2A-like sequence, to truncated human CD19 that serves as selectable marker. AP1903-inducible activation of the Caspase 9 suicide gene is achieved by expressing a chimeric protein (iC9), fused to a drug-binding domain derived from human FK506-binding protein (FKBP). The iC9 is quiescent inside cells until exposure to AP1903, which cross-links the FKBP domains, initiates iCasp9 signaling, and induces apoptosis of the gene-modified cells. The gene and AP1903 will be supplied by Bellicum Pharmaceuticals (Houston, TX), which will also assist with functional studies. The use of this construct has been described (6, 7) and will be used to conduct functional studies in NSG mice to optimize dosing to induce rapid apoptosis in systemic and intracranial DRI-CAR T cells.

Lentivirus site integration analysis will initially be performed in our laboratory using the Lenti-X™ System (Clontech) using GenomeWalker technology.

Example 3—Standardization of Cell Manufacturing and Release Criteria for Use of DRI-CAR for Human Therapy The cytotoxicity (potency and toxicological) assays, flow cytometric graft composition analysis, and infectious disease testing for cGMP cell manufacturing that will enable translation to clinical trials. For cell and gene therapy products, release criteria as defined by FDA in 21 CFR 211.165 and 610 for sterility, purity, identity, and potency are required. FDA mandates procedures for sterility testing. Identity testing will be accomplished by clinical HLA typing. Purity/composition of the cell product and potency testing will require standardization in our laboratory. FDA regulation 21 CFR 600.3 requires that the specific ability of a product to function as indicated should be defined by an appropriate laboratory test, and 21 CFR 610.10 states that assessment of potency should consist of either in vitro and/or in vivo tests specifically designed for the product. FDA also recommends that cytotoxicity be correlated with target phenotype; therefore, the cytotoxicity will be validated using a defined target glioma cell line of consistent passage number as standard for evaluation of DRI-CAR graft function to clinical requirements as defined in the Clinical Laboratory Improvement Act of 1988 (CLIA) for Laboratory Developed Tests. Optimal function will be provisionally defined as 50% killing at a 20:1 E:T (efector:target) ratio. Cultured astrocytes will serve as negative targets and K562 erythroleukemia cell targets as positive targets. Final purity and composition will be evaluated by flow cytometry for % total T cells (CD3), % γδ T cells, % αβ T cells (CD3+CD4+γδ− and % CD3+CD8+γδ−), % NK cells (CD16/56), % B cells (CD19) and % monocytes (CD14). Target release criteria are ≥60% γδ T cells, ≤5% αβ T cells, and ≤25% NK cells. Statistical analysis will consist of establishing a mean, SD, and 95% CI for individual cell phenotypes in the purity/composition analysis and for each % killing for each E:T ratio in the functional assay in a minimum of 20 assays. ANOVA will be used to compare differences in individual E:T ratios between groups. The in vitro cytotoxic function as well as migration studies and survival outcomes in animal model will be incorporated.

Example 4—Evaluation of the Safety, Toxicity, Trafficking, and Migration Potential of CAR-DRI $^{111}$[In]-Labeled γδ T Cells as Post-Resection Cell Therapy in Three Patients with Primary Glioblastoma in a Phase 0 Clinical Trial A small number of initial experiments using $^{111}$[In]-labeled DRI-CAR T cells to verify TMZ resistance under clinical conditions and migration to potential areas of residual microscopic disease will be conducted. This study will be conducted as a Phase 0 clinical trial in which toxicity is the endpoint of primary interest. Eligible patients will be entered sequentially and be given one infusion. Frequencies of side effects will be summarized by body system, grade and causality by using frequencies and percentages. Individual subject listing will be provided which includes the above information, plus study day of symptom onset and length of adverse event. No statistical comparisons will be made. Secondary objectives will include monitoring of time to progression, presence of early and late systemic hematopoietic chimerism, systemic immune function and overall survival for the purpose of hypothesis generation and design of Phase I and II clinical trials. Up to 3 evaluable patients will be enrolled consisting of adult males and non-pregnant females at least 18 years of age undergoing resection for a histologically confirmed primary GBM. Patients will undergo a single leukapheresis following resection and prior to initiation of RT (radiation therapy)+TMZ therapy for DRI-CAR manufacturing. A single dose of 1×10$^6$/kg DRI-CAR T cells will be administered during high-dose TMZ therapy following the rest period at the terminus of combined RT+TMZ. A portion of the cell product will be labeled with $^{111}$[In] to follow migration of the cells. Single photon emission computerized tomography (SPECT) will be performed 12, 24, and 48 hours post-infusion. A single experienced nuclear medicine physician will review all attenuation-corrected $^{111}$[In]-oxine-labeled leukocyte planar and SPECT images. Individual patients will be followed for at least 30 days for toxicity prior to enrolling the next patient. The Cancer Therapy Evaluation Program Common Toxicity Criteria for the grading of adverse events will be used to define any Grade 3 or 4 toxicity involving the liver, lungs and heart, or any other Grade 4 toxicity as a dose-limiting toxicity (DLT) if it is deemed possibly or probably related to DRI-CAR T cells. Important additional events that will be considered DLT if they are possibly or probably related include death, stroke, hematoma requiring surgery, untreatable neurologic deterioration, unresponsive systemic infection, and graft vs. host disease. Presumptive off-target toxicity or intra-cranial events such as inflammation or leukoencephalopathy will trigger AP1903 administration to activate apoptosis of DRI-CAR T cells via the iC9 suicide gene.

Example 5—Expression of Stress-Induced Antigens

Figure 4A:
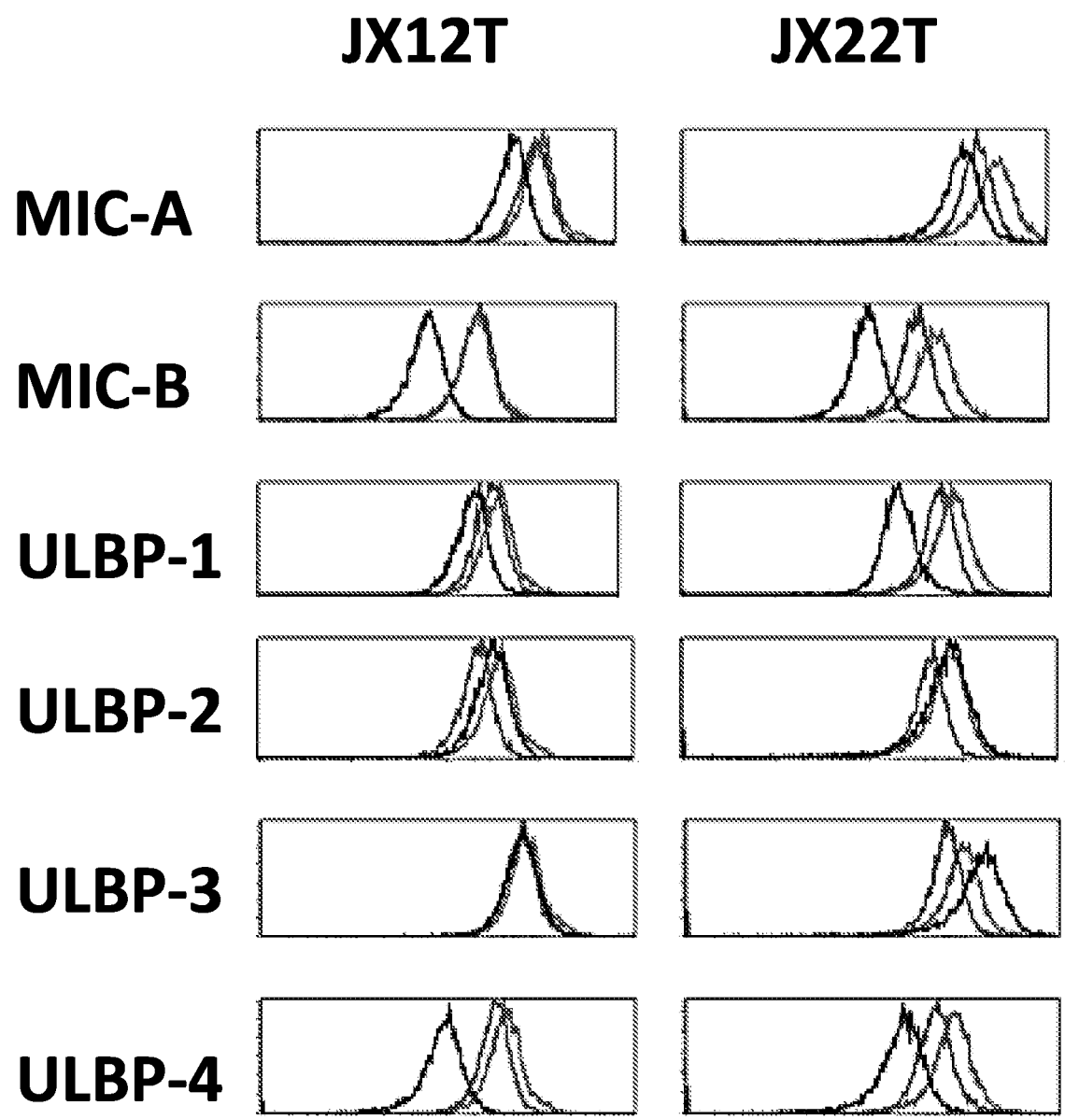
FIG. 4A shows stress-associated NKG2DL expression on X12T and X22T glioma xenografts. Both cell types showed autofluorescence. Black=isotype control, blue=tumor, red=tumor exposed to 400 μM TMZ for 4 h.
Figure 4B:
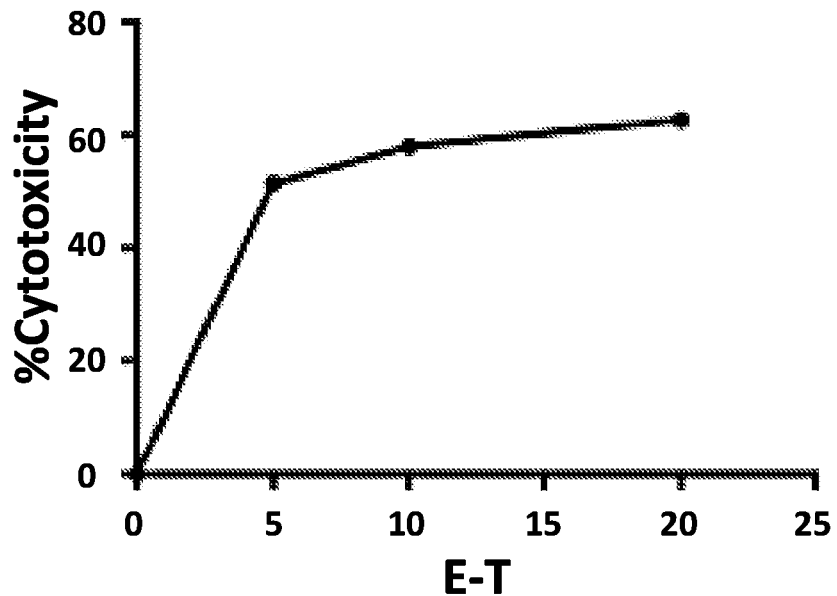
FIG. 4B shows ex vivo expanded/activated γδ T cells modified to be resistant to TMZ were cytotoxic to cells derived from X12T and X22T glioma xenograft in vitro ultured with increasing Effector:Target (E:T) ratios of X12T and X22T and % Lysis expressed as live/dead ratio by flow cytometry.
Figure 4B:
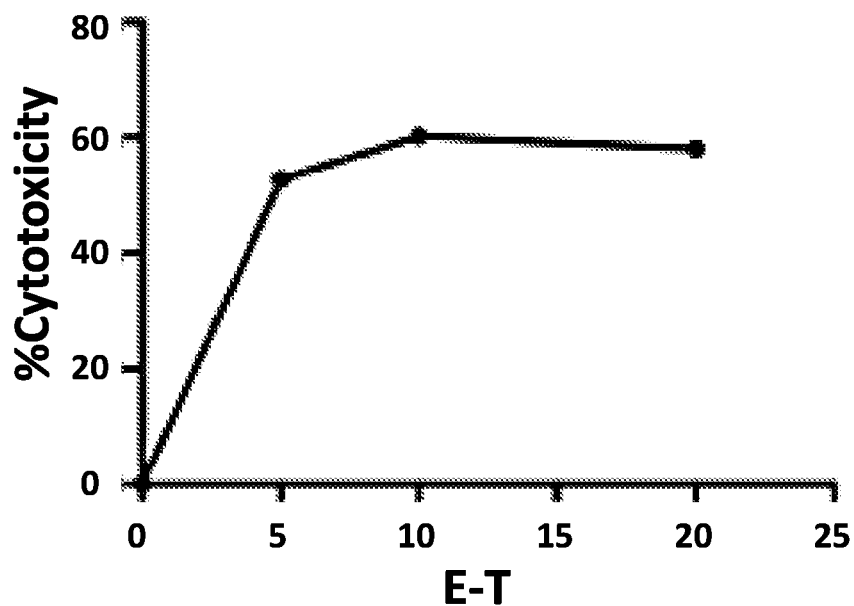

Selected stress-induced ligands (NKG2DL) in glioma xenografts are upregulated upon exposure to TMZ (FIG. 4A). FIG. 4 shows expression of the NKG2DLs MIC-A, MIC-B, ULBP-1, ULBP-2, ULBP-3 and ULBP-4 in X12T and X22T glioma xenografts. X12T glioma xenografts show expression of MIC-A, ULBP-1 and ULBP-4 with minimal upregulation following treatment with 400 μM TMZ for 4 hours. X22T glioma xenografts show expression of MIC-A, MIC-B, ULBP-1 and ULBP-4 with upregulation of MIC-A and ULBP-4 following treatment with 400 μM TMZ for 4 hours. Ex vivo expanded/activated γδ T cells were effective in killing cells derived from X12T and X22T glioma xenografts as shown in FIG. 4B. 4. γδ T cells modified to express a survival factor for TMZ resistance were cultured at increasing Effector:Target (E:T) ratios with cells derived from X12T and X22T glioma xenograft and the percent lysis (determined by the ratio of live to dead cells as determined by flow cytometry) expressed a function of the E:T ratio. At E:T ratios greater than 10:1, the γδ T cells were cytotoxic to the X12T and X22T glioma xenograft derived cells. The γδ T cells showed no evidence of toxicity against cultured human astrocytes at an E:T ratio of 20:1.

Figure 2:
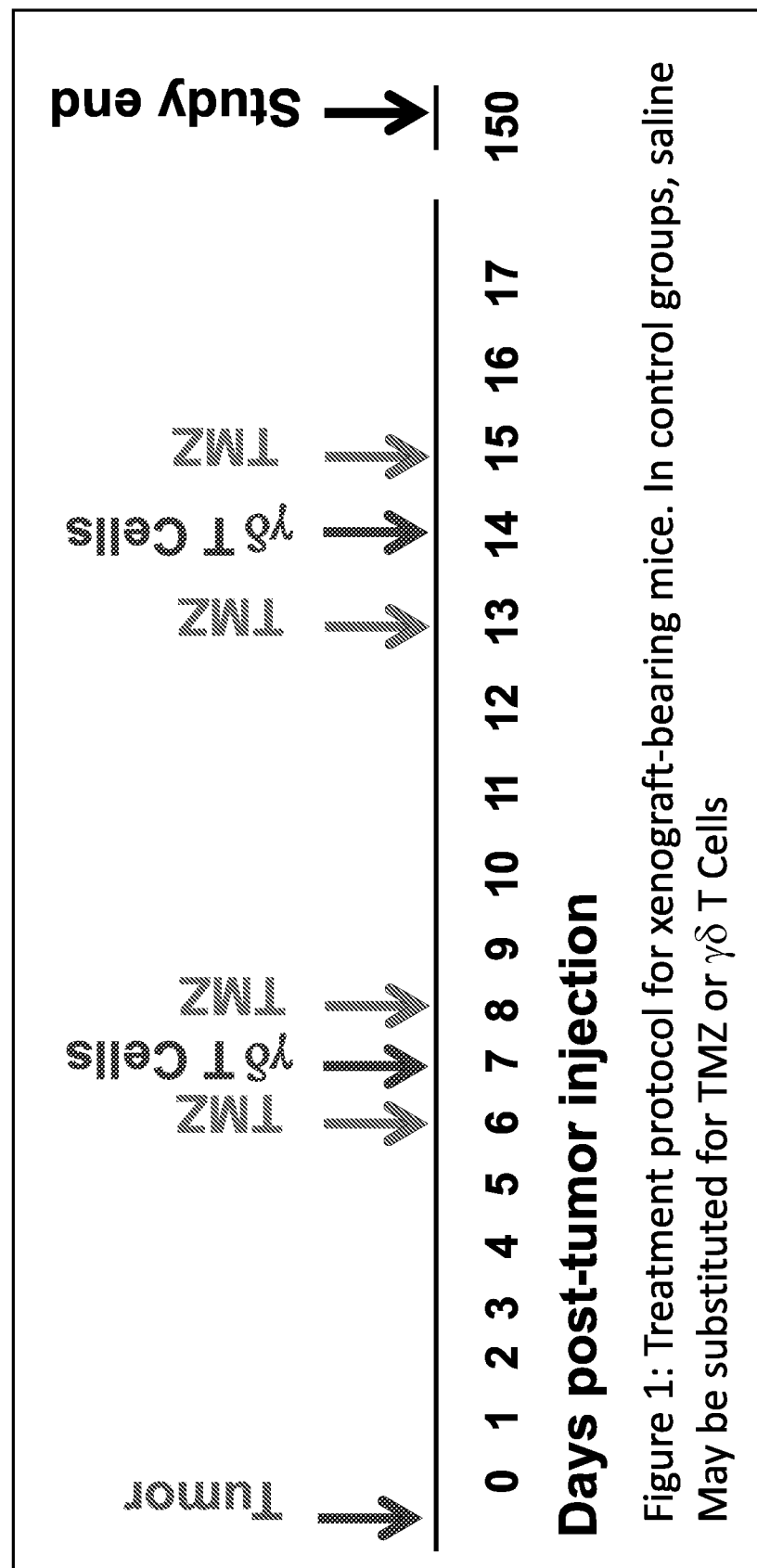
FIG. 2 shows exemplary experimental design for treatment.
Figure 3:
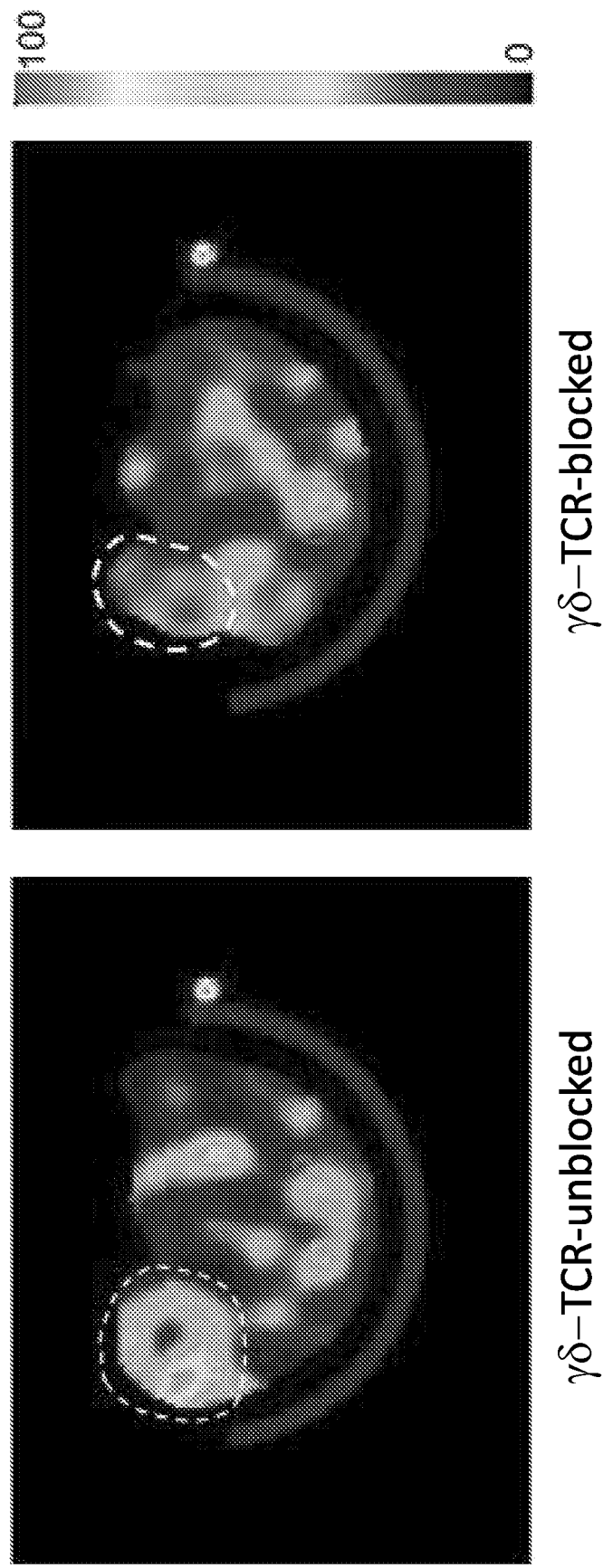
FIG. 3A shows SPECT/CT fused images (axial view) showing distribution of $^{111}$[In]-labeled γδT cells in 4T1 mammary fat pad tumors at 48 h post injection performed using γδT cells that were untreated and illustrates the untreated γδT cells bound the tumor; the dotted circle delineates the tumor region.
FIG. 3B shows the same imaging described in FIG. 3A performed using γδT cells that were pretreated with an anti-γδ TCR monoclonal antibody prior to injection and illustrates the treated γδT cells did not bind the tumor; the dotted circle delineates the tumor region.
Figure 5A:
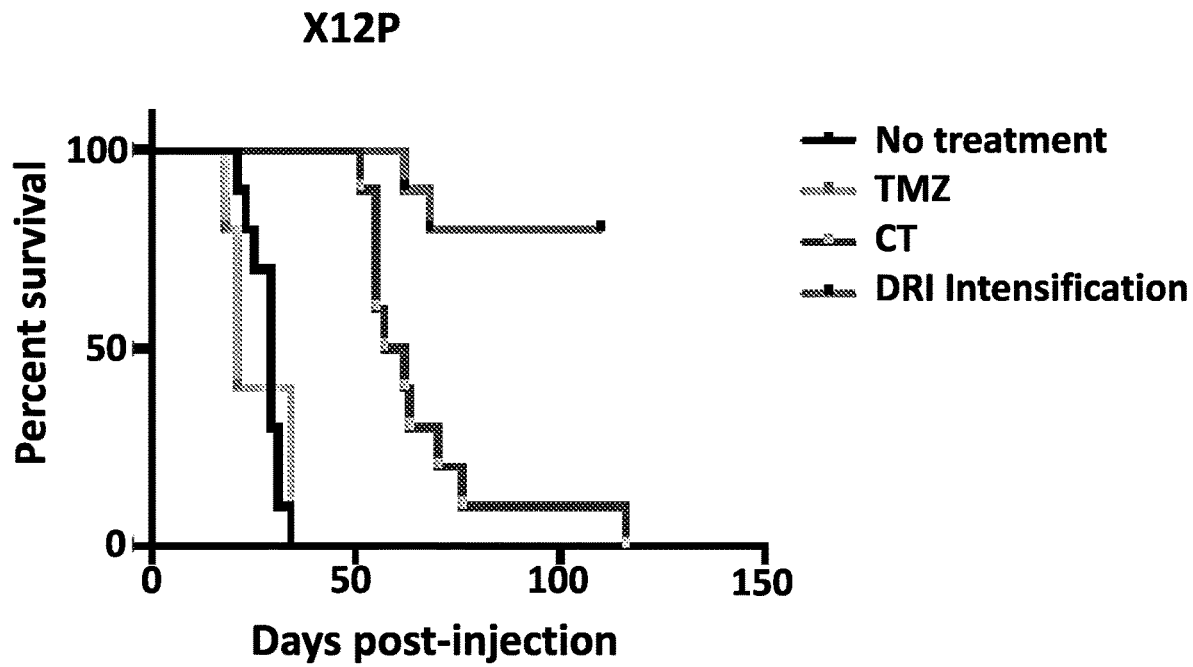
FIG. 5A shows survival of X12P glioma-bearing mice following treatment with TMZ alone (TMZ), with the combination of TMZ plus a composition comprising γδ T cells and NK cells modified to express a survival factor for TMZ resistance (DRI), with unmodified γδ T cells and NK cells (CT) and in control mice receiving no treatment.
Figure 5B:
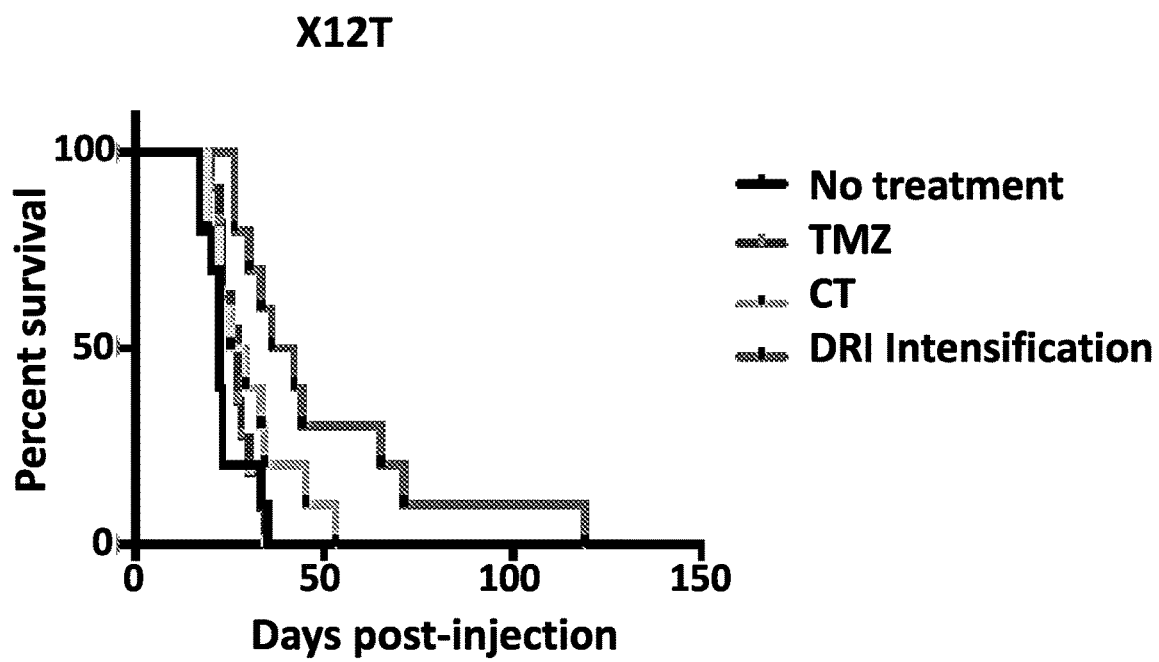
FIG. 5B shows survival of X12T glioma-bearing mice following treatment with TMZ alone (TMZ), with the combination of TMZ plus a composition comprising γδ T cells and NK cells modified to express a survival factor for TMZ resistance (DRI), with unmodified γδ T cells and NK cells (CT) and in control mice receiving no treatment.

Example 6—Effectiveness of γδ T Cell Therapy is Increased by Expression of Stress-Induced Antigens The expression of NKG2DL on tumor cells increases the overall potency of γδ T cell therapy. FIGS. 5A and 5B show the survival of X12P and X12T (TMZ resistant) glioma-bearing mice, respectively, in response to various treatments. FIG. 5A shows survival of X12P glioma-bearing mice treated with TMZ alone (TMZ), the combination of TMZ plus a composition comprising γδ T cells and NK cells modified to express a survival factor for TMZ resistance (DRI), mice receiving unmodified γδ T cells and NK cells (CT) and in control mice receiving no treatment. The TMZ treatment regimen (blue) and the DRI treatment regimen (red) increased survival of X12P glioma-nearing mice as compared to the CT treatment regimen (green) and untreated mice (black) (p<0.001). The DRI treatment regimen increased median survival from 57 to 75 days over the TMZ treatment regimen. FIG. 5B shows survival of X12T glioma-bearing mice treated as described in FIG. 5A. The DRI treatment regimen (red) increased survival in X12T glioma-bearing mice as compared to untreated mice (black) (p=0.0147). The TMZ treatment regimen did not improve survival in X12T glioma bearing mice as compared to untreated mice as expected. The DRI treatment regimen increased median survival from 22 to 27 days over the TMZ treatment regimen. The effect of the DRI treatment regimen could be increased by intensification of the administration of the γδ T cells and NK cells from a single administration per week (as shown in FIG. 2) to two administrations per week (data not shown). In this modified administration, the DRI treatment regimen increased survival in X12T glioma-bearing mice as compared to untreated mice (p=0.0004) and increased median survival from 22 to 38 days over the TMZ treatment regimen.

Example 7—Stress-Induced Antigens are not Up-Regulated in Normal Brain Tissue

Figure 6:
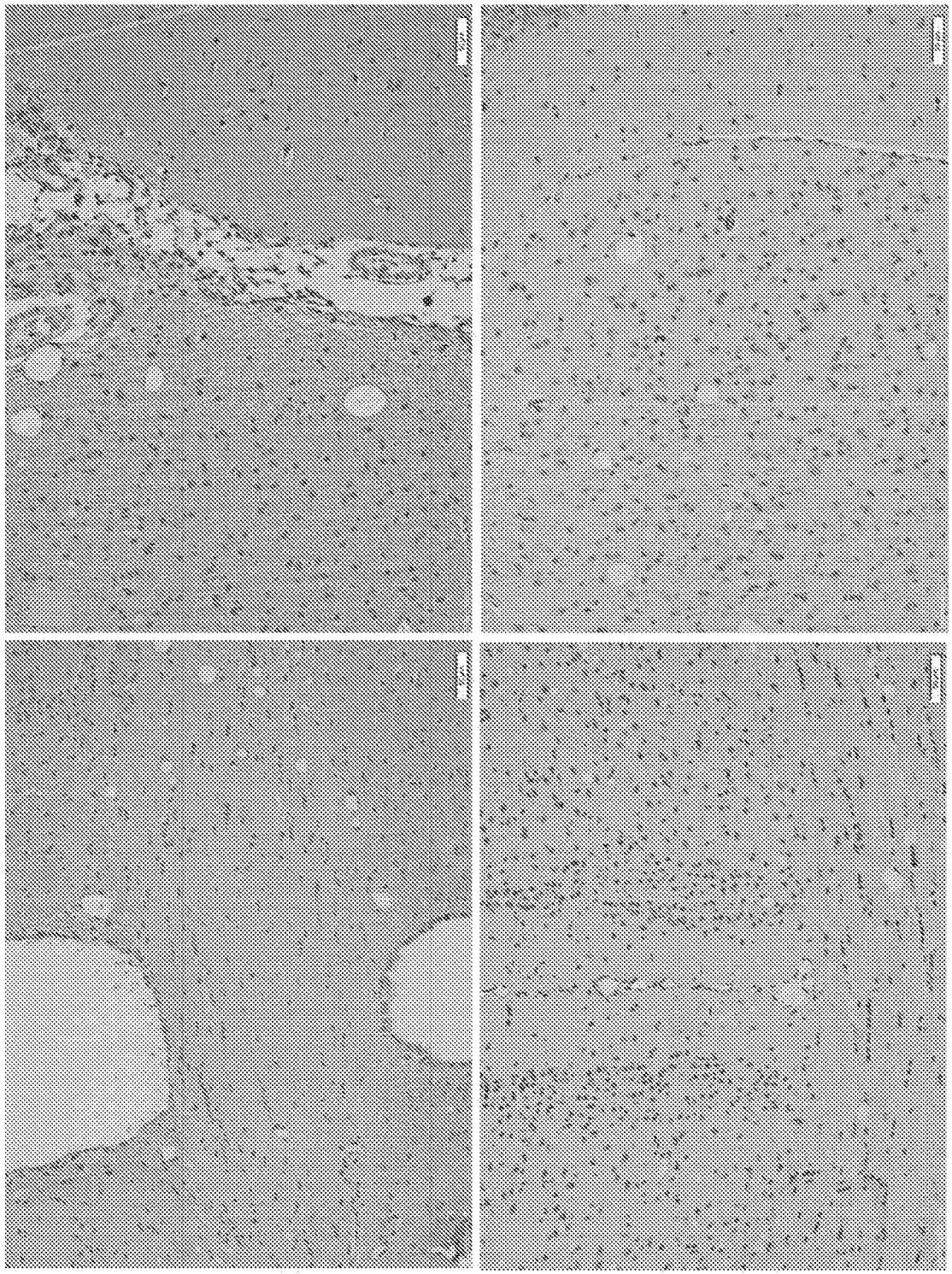
FIG. 6 shows stress-induced antigen expression is not increased in normal brain tissue adjacent to metastatic brain tumor tissue.

Observation of radiated metastatic brain tumor tissue and adjacent normal brain tissue reveals stress-induced antigen (NKG2D ligand) upregulation in tumor tissue with essentially no expression in normal (i.e., non-tumor) surrounding brain tissue (FIG. 6). FIG. 6 shows stress-induced antigen expression from radiated metastatic brain tumor tissue and adjacent normal brain tissue. Metastatic brain tumor tissue showed strong expression of ULBP-1 and mild expression of ULBP-2 and ULBP-3. No stress-induced antigen expression was observed in adjacent normal brain tissue. As such, off-target effects and resulting injury to normal brain tissue by cell compositions described herein are not likely.

Example 8—Stress-Induced Antigens are not Up-Regulated by Radiation Treatment

Figure 7:
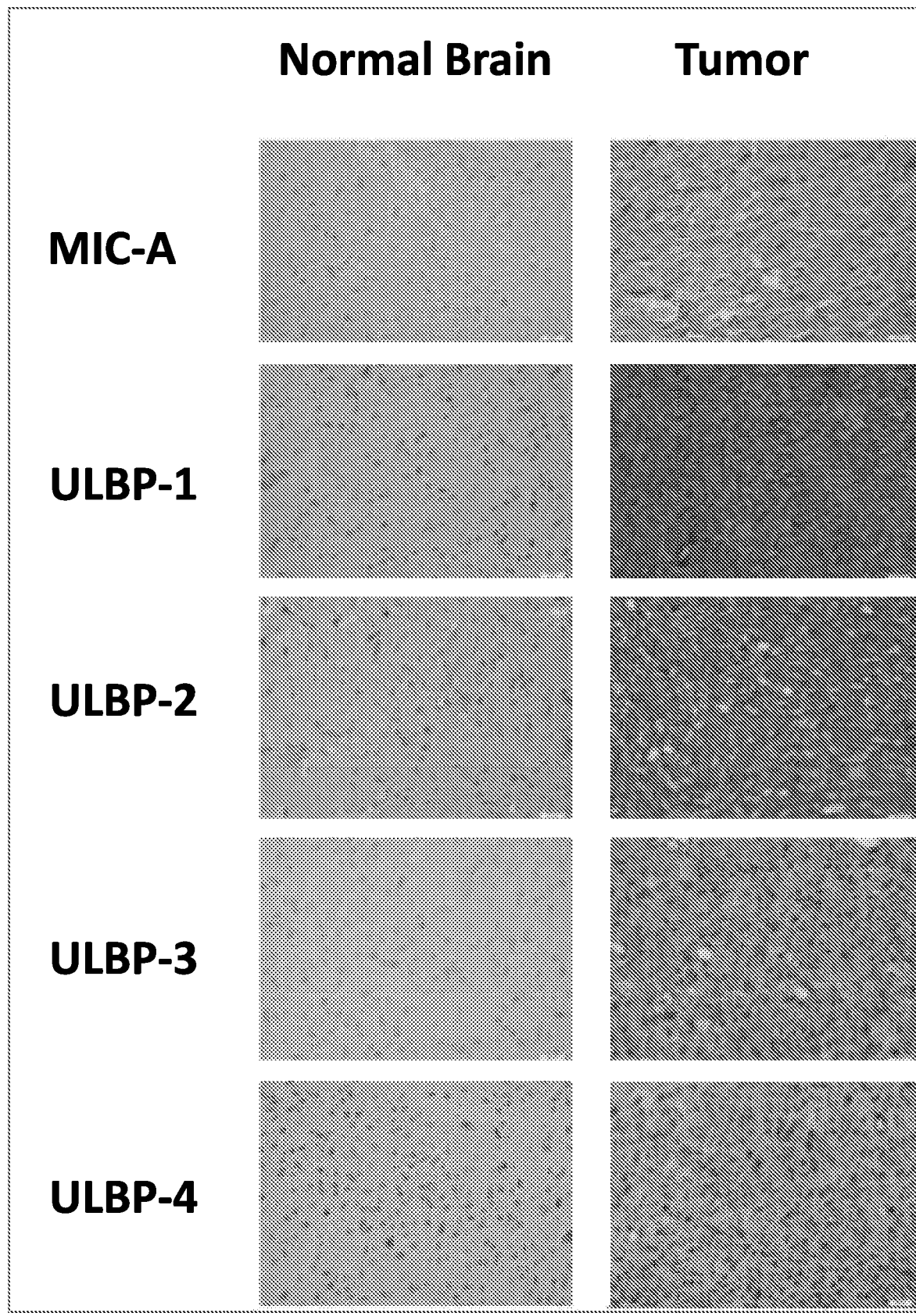
FIG. 7 shows stress-induced antigen expression is not increased in normal brain tissue after radiation treatment.

Similarly, stress-induced antigen (NKG2D ligand) are not upregulated in irradiated mouse brain nor are other signs of inflammation visible (FIG. 7). FIG. 7 shows whole brain of WT C56BL/6 mice (panels b, d) radiated using an anterior-posterior and posterior-anterior pair of beams of 160 kV X-rays at a dose of 17Gy and control mice (panels a, c) receiving no radiation. Mice were killed and brains harvested at 70 days. Panels a and b compare stress antigen MULT-1 staining between control and radiated mice. Panels c and d compare staining with anti-CD3 between control and radiated mice. Radiated mice are negative for both MULT-1 and anti-CD3 showing that stress-induced antigens are not upregulated in response to radiation treatment in normal brain tissue and lymphocyte infiltration is not induced in response to radiation treatment in normal brain tissue.

LITERATURE CITED

1. Bryant N L, Suarez-Cuervo C, Gillespie G Y, Markert J M, Nabors L B, Meleth S, Lopez R D, Lamb L S, Jr. Characterization and immunotherapeutic potential of gammadelta T-cells in patients with glioblastoma. Neuro Oncol. 2009; 11(4):357-67. PubMed PMID: 19211933; PubMed Central PMCID: PMCPMC2743216.
2. Lamb L S, Jr. gammadelta T cells as immune effectors against high-grade gliomas. Immunol Res. 2009; 45(1): 85-95. PubMed PMID: 19711198.
3. Bryant N L, Gillespie G Y, Lopez R D, Markert J M, Cloud G A, Langford C P, Arnouk H, Su Y, Haines H L, Suarez-Cuervo C, Lamb L S, Jr. Preclinical evaluation of ex vivo expanded/activated gammadelta T cells for immunotherapy of glioblastoma multiforme. Journal of neuro-oncology. 2011; 101(2):179-88. Epub 2010/06/10. doi: 10.1007/s11060-010-0245-2. PubMed PMID: 20532954.
4. Lamb L S, Jr., Bowersock J, Dasgupta A, Gillespie G Y, Su Y, Johnson A, Spencer H T. Engineered drug resistant gammadelta T cells kill glioblastoma cell lines during a chemotherapy challenge: a strategy for combining chemo- and immunotherapy. PLoS One. 2013; 8(1): e51805. Epub 2013/01/18. doi: 10.1371/journal.pone.0051805. PubMed PMID: 23326319; PubMed Central PMCID: PMC3543433.
5. Beck B H, Kim H G, Kim H, Samuel S, Liu Z, Shrestha R, Haines H, Zinn K, Lopez R D. Adoptively transferred ex vivo expanded gammadelta-T cells mediate in vivo antitumor activity in preclinical mouse models of breast cancer. Breast cancer research and treatment. 2010; 122 (1):135-44. Epub 2009/09/19. doi: 10.1007/s10549-009-0527-6. PubMed PMID: 19763820; PubMed Central PMCID: PMC2883655.
6. Zhou X, Di Stasi A, Tey S K, Krance R A, Martinez C, Leung K S, Durett A G, Wu M F, Liu H, Leen A M, Savoldo B, Lin Y F, Grilley B J, Gee A P, Spencer D M, Rooney C M, Heslop H E, Brenner M K, Dotti G. Long-term outcome after haploidentical stem cell transplant and infusion of T cells expressing the inducible caspase 9 safety transgene. Blood. 2014; 123(25):3895-905. Epub 2014/04/23. doi: 10.1182/blood-2014-01-551671. PubMed PMID: 24753538; PubMed Central PMCID: PMC4064331.
7. Di Stasi A, Tey S K, Dotti G, Fujita Y, Kennedy-Nasser A, Martinez C, Straathof K, Liu E, Durett A G, Grilley B, Liu H, Cruz C R, Savoldo B, Gee A P, Schindler J, Krance R A, Heslop H E, Spencer D M, Rooney C M, Brenner M K. Inducible apoptosis as a safety switch for adoptive cell therapy. N Engl J Med. 2011; 365(18):1673-83. Epub 2011/11/04. doi: 10.1056/NEJMoa1106152. PubMed PMID: 22047558; PubMed Central PMCID: PMC3236370.
8. Zitvogel L, Apetoh L, Ghiringhelli F, Kroemer G. Immunological aspects of cancer chemotherapy. Nat Rev Immunol. 2008; 8(1):59-73. PubMed PMID: 18097448.
9. Lake R A, Robinson B W. Immunotherapy and chemotherapy—a practical partnership. Nat Rev Cancer. 2005; 5(5):397-405. Epub 2005/05/03. doi: nrc1613 [pii] 10.1038/nrc1613. PubMed PMID: 15864281.
10. van der Most R G, Robinson B W, Lake R A. Combining immunotherapy with chemotherapy to treat cancer. Discov Med. 2005; 5(27):265-70. Epub 2005/06/01. PubMed PMID: 20704886.
11. Ramakrishnan R, Assudani D, Nagaraj S, Hunter T, Cho H I, Antonia S, Altiok S, Celis E, Gabrilovich D I. Chemotherapy enhances tumor cell susceptibility to CTL-mediated killing during cancer immunotherapy in mice. The Journal of clinical investigation. 2010; 120(4):1111-24. Epub 2010/03/18. doi: 10.1172/JCI40269. PubMed PMID: 20234093; PubMed Central PMCID: PMC2846048.
12. Gulley J L, Madan R A, Arlen P M. Enhancing efficacy of therapeutic vaccinations by combination with other modalities. Vaccine. 2007; 25 Suppl 2:B89-96. Epub 13. Fridlender Z G, Sun J, Singhal S, Kapoor V, Cheng G, Suzuki E, Albelda S M. Chemotherapy delivered after viral immunogene therapy augments antitumor efficacy via multiple immune-mediated mechanisms. Mol Ther. 2010; 18(11):1947-59. Epub 2010/08/05. doi: 10.1038/mt.2010.159. PubMed PMID: 20683443; PubMed Central PMCID: PMC2990510.
14. Arlen P M, Gulley J L, Parker C, Skarupa L, Pazdur M, Panicali D, Beetham P, Tsang K Y, Grosenbach D W, Feldman J, Steinberg S M, Jones E, Chen C, Marte J, Schlom J, Dahut W. A randomized phase II study of concurrent docetaxel plus vaccine versus vaccine alone in metastatic androgen-independent prostate cancer. Clinical cancer research: an official journal of the American Association for Cancer Research. 2006; 12(4):1260-9. Epub 2006/02/21. doi: 10.1158/1078-0432.CCR-05-2059. PubMed PMID: 16489082; PubMed Central PMCID: PMC1526707.
15. Ramakrishnan R, Antonia S, Gabrilovich D I. Combined modality immunotherapy and chemotherapy: a new perspective. Cancer Immunol Immunother. 2008; 57(10): 1523-9. Epub 2008/05/20. doi: 10.1007/s00262-008-0531-4. PubMed PMID: 18488219.
16. Mitchell M S. Combinations of anticancer drugs and immunotherapy. Cancer Immunol Immunother. 2003; 52(11):686-92. Epub 2003/08/28. doi: 10.1007/s00262-003-0427-2. PubMed PMID: 12942200.
17. Antonia S J, Mirza N, Fricke I, Chiappori A, Thompson P, Williams N, Bepler G, Simon G, Janssen W, Lee J H, Menander K, Chada S, Gabrilovich D I. Combination of p53 cancer vaccine with chemotherapy in patients with extensive stage small cell lung cancer. Clinical cancer research: an official journal of the American Association for Cancer Research. 2006; 12(3 Pt 1):878-87. Epub 2006/02/10. doi: 10.1158/1078-0432.CCR-05-2013. PubMed PMID: 16467102.
18. Merchant R E, Baldwin N G, Rice C D, Bear H D. Adoptive immunotherapy of malignant glioma using tumor-sensitized T lymphocytes. Neurol Res. 1997; 19(2):145-52. PubMed PMID: 9175143.
19. Plautz G E, Barnett G H, Miller D W, Cohen B H, Prayson R A, Krauss J C, Luciano M, Kangisser D B, Shu S. Systemic T cell adoptive immunotherapy of malignant gliomas. J Neurosurg. 1998; 89(1):42-51. PubMed PMID: 9647171.
20. Kruse C A, Cepeda L, Owens B, Johnson S D, Stears J, Lillehei K O. Treatment of recurrent glioma with intracavitary alloreactive cytotoxic T lymphocytes and interleukin-2. Cancer Immunol Immunother. 1997; 45(2):77-87. PubMed PMID: 9390198.
21. Read S B, Kulprathipanja N V, Gomez G G, Paul D B, Winston K R, Robbins J M, Kruse C A. Human alloreactive CTL interactions with gliomas and with those having upregulated HLA expression from exogenous IFN-gamma or IFN-gamma gene modification. J Interferon Cytokine Res. 2003; 23(7):379-93. PubMed PMID: 14511464.
22. Merchant R E, Ellison M D, Young H F. Immunotherapy for malignant glioma using human recombinant interleukin-2 and activated autologous lymphocytes. A review of pre-clinical and clinical investigations. J Neurooncol. 1990; 8(2):173-88.
23. Barba D, Saris S C, Holder C, Rosenberg S A, Oldfield E H. Intratumoral LAK cell and interleukin-2 therapy of human gliomas. J Neurosurg. 1989; 70(2):175-82. PubMed PMID: 2643685.
24. Saris S C, Patronas N J, Rosenberg S A, Alexander J T, Frank J, Schwartzentruber D J, Rubin J T, Barba D, Oldfield E H. The effect of intravenous interleukin-2 on brain water content. J Neurosurg. 1989; 71(2):169-74. PubMed PMID: 2787395.
25. Hayes R L, Koslow M, Hiesiger E M, Hymes K B, Hochster H S, Moore E J, Pierz D M, Chen D K, Budzilovich G N, Ransohoff J. Improved long term survival after intracavitary interleukin-2 and lymphokine-activated killer cells for adults with recurrent malignant glioma. Cancer. 1995; 76(5):840-52. PubMed PMID: 8625188.
26. Dillman R O, Duma C M, Schiltz P M, DePriest C, Ellis R A, Okamoto K, Beutel L D, De Leon C, Chico S. Intracavitary placement of autologous lymphokine-activated killer (LAK) cells after resection of recurrent glioblastoma. J Immunother. 2004; 27(5):398-404. PubMed PMID: 15314549.
27. Wu J, Groh V, Spies T. T cell antigen receptor engagement and specificity in the recognition of stress-inducible MHC class I-related chains by human epithelial gamma delta T cells. J Immunol. 2002; 169(3):1236-40. PubMed PMID: 12133944.
28. Poggi A, Carosio R, Fenoglio D, Brenci S, Murdaca G, Setti M, Indiveri F, Scabini S, Ferrero E, Zocchi M R. Migration of V delta 1 and V delta 2 T cells in response to CXCR3 and CXCR4 ligands in healthy donors and HIV-1-infected patients: competition by HIV-1 Tat. Blood. 2004; 103(6):2205-13. PubMed PMID: 14630801.

The invention claimed is:
1. A method of treating a subject suffering from a tumor, the method comprising:
   a. administering to the subject a cell composition comprising γδ T cells expressing at least NKG2D, a chimeric antigen receptor (CAR) directed to a tumor antigen,, and a polypeptide that confers resistance to a chemotherapeutic agent, wherein the chemotherapeutic agent increases the expression of a NKG2D ligand on the tumor; and
   b. administering to the subject the chemotherapeutic agent, wherein the chemotherapeutic agent is administered either before administration of the cell composition to the subject, after administration of the cell composition to the subject, concurrently with administration of the cell composition to the subject or any combination of the foregoing;
   wherein the CAR comprises an endodomain, and the endodomain consists of a CD3-zeta signaling domain or one costimulatory domain.
2. The method of claim 1 further comprising at least one additional administration of the cell composition to the subject.
3. The method of claim 1, wherein the chemotherapeutic agent is administered before administration of the cell composition to the subject, or concurrently with administration of the cell composition to the subject, or a combination of the foregoing.
4. The method of claim 1, wherein the cell composition is administered to the subject on day X and the chemotherapeutic agent is administered to the subject 12 to 72 hours prior to day X, 12 to 72 hours after day X or both 12 to 72 hours prior to and after day X.

5. The method of claim 1, wherein the cell composition is administered to the subject on day X and the chemotherapeutic agent is administered to the subject 12 to 72 hours prior to day X, 12 to 72 hours after day X or both 12 to 72 hours prior to and after day X, followed by an additional administration of the cell composition to the subject on day Y, with optional administration of the chemotherapeutic agent to the subject 12 to 72 hours prior to day Y, 12 to 72 hours after day Y or both 12 to 72 hours prior to and after day Y.

6. The method of claim 1, wherein the cancer is selected from the group consisting of brain cancer, breast cancer, prostate cancer, lung cancer, colon cancer, epithelial cancer, head and neck cancer, skin cancer, cancers of the genitourinary tract, ovarian cancer, endometrial cancer, cervical cancer, kidney cancer, gastric cancer, cancer of the small intestine, liver cancer, pancreatic cancer, gall bladder cancer, cancers of the bile duct, esophageal cancer, cancer of the salivary glands, thyroid cancer, and a hematologic malignancy.

7. The method of claim 1, wherein the cancer is selected from the group consisting of pineal tumors, pituitary tumors, PNET, schwannoma, lymphoma, medulloblastoma, meningioma, metastatic brain cancer, neurofibroma, neuronal & mixed neuronal-glial tumors, oligoastrocytoma, oligodendroglioma, astrocytoma, atypical teratoid rhaboid tumor (ATRT), chondrosarcoma, choroid plexus tumors, craniopharyngioma, ependymoma, germ cell tumor, neuroblastoma, glioblastoma and glioma.

8. The method of claim 1, wherein the cancer is sensitive to the chemotherapeutic agent.

9. The method of claim 1, wherein the cancer is resistant to the chemotherapeutic agent.

10. The method of claim 1, wherein the tumor antigen is selected from the group consisting of EphA2, B cell maturation antigen (BCMA), B7-H3, B7-H6, CALX, CA9, CD22, CD19, CD20, ROR1, kappa or light chain, carcinoembryonic antigen, alpha-fetoprotein, CA-125, Glypican-3, epithelial tumor antigen, melanoma-associated antigen, EGP2, EGP40, EPCAM, ERBB3, ERBB4, ErbB3/4, PAP, FAR, FBP, fetal AchR, Folate Receptor α, mutated p53, mutated ras, HER2, ERBB2, HER3, folate binding protein, HIV-1 envelope glycoprotein gp120, HIV-1 envelope glycoprotein gp41, 5T4, 8H9, GD2, CD123, CD23, CD33, CD30, CD38, CD56, c-Met, fap, mesothelin, GD3, HERV-K, IL-11Ra, IL-13Ra, CSPG4, Lewis-Y, MCSP, Mucl, Muc16, NCAM, NKG2D ligands, NY-ESO-1, PRAME, PSCA, PSC1, PSMA, EGFR, Sp17, SURVIVIN, TAG72, TEM1, TEM8, EGFRvIII and VEGFR2.

11. The method of claim 1, wherein the cancer is glioblastoma and the tumor antigen is selected from the group consisting of ULBP-1, ULBP-2, ULBP-3, ULBP-4, ULBP-5, ULBP-6, MIC-A, MIC-B, EGFRvIII and IL13Rα.

12. The method of claim 1, wherein the cancer is glioblastoma and the tumor antigen is EGFRvIII or IL13Rα.

13. The method of claim 1, wherein the cancer is neuroblastoma and the tumor antigen is selected from the group consisting of ULBP-1, ULBP-2, ULBP-3, ULBP-4, ULBP-5, ULBP-6, MIC-A, MIC-B and GD2.

14. The method of claim 1, wherein the cancer is neuroblastoma and the tumor antigen is GD2.

15. The method of claim 1, wherein the cell composition further comprises at least one of αβ T cells and NK cells.

16. The method of claim 1, wherein the cell composition further comprises αβ T cells and NK cells.

17. The method of claim 1, wherein the γδ T cells are present at greater than or equal to 60% of the total cell population, αβ T cells are present at less than or equal to 5% of the total cell population and NK cells are present at less than or equal to 25% of the total cell population, as measured by flow cytometry.

18. The method of claim 1, wherein the chemotherapeutic agent is a nucleoside-analog, alkylating agent, antimetabolite, antibiotic, topoisomerase inhibitor, mitotic inhibitor, differentiating agent, or hormone therapy agent.

19. The method of claim 1, wherein the polypeptide is $O^6$-Methylguanine-DNA methyltransferase, multidrug resistance protein 1 or 5' nucleotidase II.

20. The method of claim 1, wherein the chemotherapeutic agent is an alkylating agent and the polypeptide is $O^6$-Methylguanine-DNA methyltransferase.

21. The method of claim 1, wherein the chemotherapeutic agent is temozolomide and the polypeptide is $O^6$-Methylguanine-DNA methyltransferase.

22. The method of claim 1, wherein the γδ T cells are engineered to express the CAR directed to a tumor antigen and the polypeptide, and the receptor for NKG2D is naturally present on the γδ T cells.

23. The method of claim 1, wherein the γδ T cells further express a suicide gene.

24. The method of claim 1, wherein the chemotherapeutic agent increases the expression of a NKG2D ligand selected from the group consisting of ULBP-1, ULBP-2, ULBP-3, ULBP-4, ULBP-5, ULBP-6, MIC-A and MIC-B.

25. The method of claim 1, wherein the γδ T cells are obtained from the subject and optionally expanded ex vivo.

26. The method of claim 1, wherein the cancer is glioblastoma and the tumor antigen is a NKG2D ligand.

27. The method of claim 1, wherein the endodomain consists of the CD3-zeta signaling domain.

28. The method of claim 1, wherein the endodomain consists of one co-stimulatory domain.

29. The method of claim 28, wherein the co-stimulatory domain is selected from the group consisting of CD28, 41BB, DAP10, OX40 and ICOS.

30. The method of claim 6, wherein the hematologic malignancy is selected from the group consisting of leukemia, lymphoma, multiple myeloma, and myelodysplastic syndrome.

* * * * *